(12) United States Patent
Ho

(10) Patent No.: US 7,897,643 B2
(45) Date of Patent: Mar. 1, 2011

(54) BIPHENYL CARBOXYLIC ACIDS AND DERIVATIVES THEREOF

(75) Inventor: Chih Yung Ho, Lansdale, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 12/238,549

(22) Filed: Sep. 26, 2008

(65) Prior Publication Data

US 2009/0105344 A1 Apr. 23, 2009

Related U.S. Application Data

(60) Provisional application No. 60/980,587, filed on Oct. 17, 2007.

(51) Int. Cl.
*A61K 31/19* (2006.01)
*C07C 63/331* (2006.01)
(52) U.S. Cl. .................................. 514/570; 562/469
(58) Field of Classification Search .................. None
See application file for complete search history.

(56) References Cited

U.S. PATENT DOCUMENTS 5,877,399 A 3/1999 Hsiao et al.

FOREIGN PATENT DOCUMENTS

| EP | 1650183 A | 4/2006 |
|---|---|---|
| WO | WO 01/78721 | 10/2001 |
| WO | WO 03/008635 | 1/2003 |
| WO | WO 2006/004555 | 1/2006 |
| WO | WO 2006005554 | 5/2006 |

OTHER PUBLICATIONS

Citron, M., et al. "Mutant Presenilins of Alzheimer's Disease Increase Production of 42-Residue Amyloid β-Protein in Both Transfected Cells and Transgenic Mice", Nature Medicine, vol. 3, No. 1, 1997, pp. 67-72.
During, M., et al. "Controlled Release of Dopamine from a Polymeric Brain Implant: In Vivo Characterization", (Abstract) Annals of Neurology, vol. 25, Issue 4, pp. 351-356.
Eriksen, J., et al. NSAIDs and Enantiomers of Flurbiprofen Target γ-secretase and Lower Aβ42 In Vivo, Journal of Clinical Investigation, vol. 112, No. 3, (2003) pp. 440-449.
Ida, N., et al. "Analysis of Heterogeneous βA4 Peptides in Human Cerebrospinal Fluid and Blood by a Newly Developed Sensitive Western Blot Assay", Journal of Biological Chemistry, vol. 271k No. 37, (19960, pp. 22908-22914.
Irizarry, M., et al., "APPSW Transgenic Mice Developed Age-Related A Deposits and Neuropil Abnormalities", Journal of Neuropathology & Experimental Neurology 56(9): 965-973 (1997) Abstract.
Kawabayashi, T., et al. "Age-Dependent Changes in Brain, CSF, and Plasma Amyloid βProtein in the Tg2576 Transgenic Mouse model of Alzheimer's Disease", Journal of Neuroscience, 21(2): pp. 372-381 (2001).

Langer, R., "New Methods of Drug Delivery", Science, vol. 249, Issue 4976, pp. 1527-1533 (1990) Abstract.
Larner, A. Secretases as Therapeutic Targets in Alzheimer's Disease: Patents 200-2004, Expert Opinion ther. Patents (2004), 14(10), pp. 1403-1420.
Levy, R., et al. "Inhibition of Calcification of Bioprosthetic Heart Valves by Local Controlled-Release Diphosphonate", Science, vol. 228, Issue 4969, pp. 190-192 (1985) (Abstract).
Lim, G.P., et al. "Ibuprofen Suppresses Plaque Pathology and Inflammation in a Mouse Model for Alzheimer's Disease", Journal of Neuroscience, 20(15): 5709-5714 (2000).
Marjaux, E., et al. "γ-Secretase Inhibitors: Still in the Running a Alzheimer's Therapeutics", Drug Discovery Today: Therapeutic Strategies, vol. 1, No. 1, (2004) p.
Morihara, T., et al. "Selective Inhibition of Aβ42 Production by NSAID R-Enantiomers", Journal of Neurochemistry, 83, pp. 1009-1012 (2002).
Peretto, I., et al. "Synthesis and Biological Activity of Flurbiprofen Analogues as Selective Inhibitors of β-Amyloidi$_{1-42}$ Secretion", J. Med. Chem. 48, pp. 5705-5720 (2005).
Saudek, C., et al. "A Preliminary Trial of the programmable Implantable Medication System for Insulin Delivery", New England Journal of Medicine, vol. 321:574-579, No. 9 (1989) Abstract.
Shimizu, K., et al. "Binding of Delta, Jagged1, and Jagged1 to Notch1 Rapidly Induces Cleavage, Nuclear Translocation, and Hyperphosphorylation of Notch2", Molecular and Cellular Biology, pp. 6913-6922 (2000).
Steiner, H., et al. "Uncovering γ-Secretase", Current Alzheimer Research, 175-181 (2004).

(Continued)

*Primary Examiner*—Paul A Zucker
(74) *Attorney, Agent, or Firm*—Woodcock Washburn LLP

(57) ABSTRACT

The present disclosure relates to compounds having the general Formula (I) with the definitions of $R_1$, $R_2$, $R_3$, and $R_4$ as provided herein, and/or salts thereof. The disclosure also relates to the use of such compounds for the treatment of Alzheimer's disease, and for the modulation of γ-secretase activity.

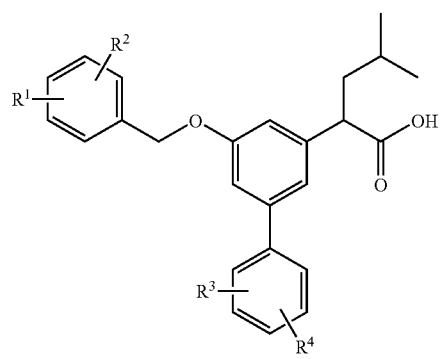

6 Claims, No Drawings

OTHER PUBLICATIONS

Wang, R., et al. "The Profile of soluble amyloid βProtein in Cultured Cell Media", Journal of Biological Chemistry, pp. 31894-31902 (1996).

Weggen, S., et al. "A subset of NSAIDs Lower Amyloidegenic Aβ42 Independently of Cyclooxygenase Activity", Letters to Nature, vol. 414, * Nov. (2001) pp. 212-216.

Vassar, R., et al. "β-Secretase Cleavage of Alzheimer's Amyloid Precursor Protein by the Transmembrane Aspartic Protease BACE", Science, vol. 286, No. 5440, pp. 735-741 (1999).

Yan, R., et al "Membrane-Anchored Aspartyl Protease with Alzheimer's Disease β-Secretse Activity", Letters to nature, vol. 42, pp. 533-537 (1999).

Yan, Q., et al. Anti-Inflammatory Drug Therapy Alters β-Amyloid Processing and Deposition in an Animal Model of Alzheimer's Disease, Journal of Neuroscience, 23(20): 7504-7509 (2003).

Xia, W., et al. "Presenilin 1 Regulates the Processing of β-Amyl lid Precursor Protein C-Terminal Fragments and the Generation of Amyloid β-Protein in Endoplasmic Reticulum and Golgi", Biochemistry 37, pp. 16465-16471 (1998).

US 7,897,643 B2

BIPHENYL CARBOXYLIC ACIDS AND DERIVATIVES THEREOF

CROSS REFERENCE TO RELATED APPLICATIONS

This application claims priority of the benefits of the filing of U.S. Provisional Application Ser. No. 60/980,587, filed Oct. 17, 2007. The complete disclosures of the aforementioned related U.S. patent application is/are hereby incorporated herein by reference for all purposes.

FIELD OF THE INVENTION

The present invention relates to compounds having the general Formula I with the definitions of $R_1$-$R_4$ given below, and/or a salt or ester thereof.

Furthermore, the invention relates to the use of said compounds for the treatment of Alzheimer's disease and their use for the modulation of γ-secretase activity. The present application is directed to a subset of a pending genus of compounds, disclosed in application WO 2006/04555 A1.

BACKGROUND OF THE INVENTION

Alzheimer's Disease (AD) is a progressive neurodegenerative disorder marked by loss of memory, cognition, and behavioral stability. AD afflicts 6-10% of the population over age 65 and up to 50% over age 85. It is the leading cause of dementia and the third leading cause of death after cardiovascular disease and cancer. There is currently no effective treatment for AD. The total net cost related to AD in the U.S. exceeds $100 billion annually.

AD does not have a simple etiology, however, it has been associated with certain risk factors including (1) age, (2) family history (3) and head trauma; other factors include environmental toxins and low level of education. Specific neuropathological lesions in the limbic and cerebral cortices include intracellular neurofibrillary tangles consisting of hyperphosphorylated tau protein and the extracellular deposition of fibrillar aggregates of amyloid beta peptides (amyloid plaques). The major component of amyloid plaques are the amyloid beta (A-beta, Abeta or Aβ) peptides of various lengths. A variant thereof, which is the Aβ1-42-peptide (Abeta-42), is believed to be the major causative agent for amyloid formation. Another variant is the Aβ1-40-peptide (Abeta-40). Amyloid beta is the proteolytic product of a precursor protein, beta amyloid precursor protein (beta-APP or APP).

Familial, early onset autosomal dominant forms of AD have been linked to missense mutations in the β-amyloid precursor protein (β-APP or APP) and in the presenilin proteins 1 and 2. In some patients, late onset forms of AD have been correlated with a specific allele of the apolipoprotein E (ApoE) gene, and, more recently, the finding of a mutation in alpha2-macroglobulin, which may be linked to at least 30% of the AD population. Despite this heterogeneity, all forms of AD exhibit similar pathological findings. Genetic analysis has provided the best clues for a logical therapeutic approach to AD. All mutations, found to date, affect the quantitative or qualitative production of the amyloidogenic peptides known as Abeta-peptides (Aβ), specifically Aβ42, and have given strong support to the "amyloid cascade hypothesis" of AD (Tanzi and Bertram, 2005, Cell 120, 545). The likely link between Aβ peptide generation and AD pathology empha sizes the need for a better understanding of the mechanisms of Aβ production and strongly warrants a therapeutic approach at modulating Aβ levels.

The release of Aβ peptides is modulated by at least two proteolytic activities referred to as β- and γ-secretase cleaving at the N-terminus (Met-Asp bond) and the C-terminus (residues 37-42) of the Aβ peptide, respectively. In the secretory pathway, there is evidence that β-secretase cleaves first, leading to the secretion of s-APPβ (sβ) and the retention of a 11 kDa membrane-bound carboxy terminal fragment (CTF). The latter is believed to give rise to Aβ peptides following cleavage by γ-secretase. The amount of the longer isoform, Aβ42, is selectively increased in patients carrying certain mutations in a particular protein (presenilin), and these mutations have been correlated with early-onset familial Alzheimer's disease. Therefore, Aβ42 is believed by many researchers to be the main culprit of the pathogenesis of Alzheimer's disease.

It has now become clear that the γ-secretase activity cannot be ascribed to a single particular protein, but is in fact associated with an assembly of different proteins.

The gamma-secretase activity resides within a multiprotein complex containing at least four components: the presenilin (PS) heterodimer, nicastrin, aph-1 and pen-2. The PS heterodimer consists of the amino- and carboxyterminal PS fragments generated by endoproteolysis of the precursor protein. The two aspartates of the catalytic site are at the interface of this heterodimer. It has recently been suggested that nicastrin serves as a gamma-secretase-substrate receptor. The functions of the other members of gamma-secretase are unknown, but they are all required for activity (Steiner, 2004. Curr. Alzheimer Research 1(3): 175-181).

Thus, although the molecular mechanism of the second cleavage-step has remained elusive until present, the γ-secretase-complex has become one of the prime targets in the search for compounds for the treatment of Alzheimer's disease.

Various strategies have been proposed for targeting gamma-secretase in Alzheimer's disease, ranging from targeting the catalytic site directly, developing substrate-specific inhibitors and modulators of gamma-secretase activity (Marjaux et al., 2004. Drug Discovery Today: Therapeutic Strategies, Volume 1, 1-6). Accordingly, a variety of compounds were described that have secretases as targets (Larner, 2004. Secretases as therapeutics targets in Alzheimer's disease: patents 2000-2004. Expert Opin. Ther. Patents 14, 1403-1420.)

Indeed, this finding was recently supported by biochemical studies in which an effect of certain NSAIDs on γ-secretase was shown (Weggen et al (2001) Nature 414, 6860, 212 and WO 01/78721 and US 2002/0128319; Morihara et al (2002) J. Neurochem. 83, 1009; Eriksen (2003) J. Clin. Invest. 112, 440). Potential limitations for the use of NSAIDs to prevent or treat AD are their inhibition activity of Cox enzymes, which can lead to unwanted side effects, and their low CNS penetration (Peretto et al., 2005, J. Med. Chem. 48, 5705-5720).

Thus, there is a strong need for novel compounds which modulate γ-secretase activity thereby opening new avenues for the treatment of Alzheimer's disease.

The object of the present invention is to provide such compounds.

SUMMARY OF THE INVENTION

The invention relates to compounds as shown in Formula I.

(Formula I)

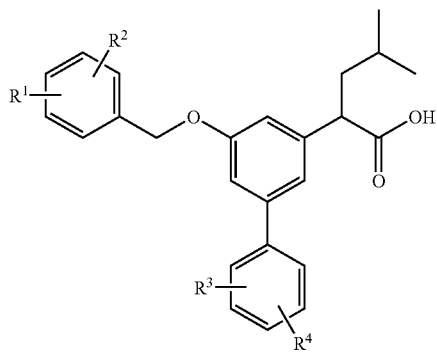

wherein:
R¹ is F, Cl, or CF₃;
R² is F, Cl, or CF₃;
R³ is F, Cl, or CF₃
R⁴ is H, F, Cl, or CF₃;

and solvates, hydrates, esters, and pharmaceutically acceptable salts thereof.

The present sub-genus of compounds, display an unexpected rise in potency and in-vivo efficacy. Specifically, the increases in potency and efficacy occur when R¹ and R² are electron withdrawing groups, such as F, Cl, or CF₃, and when the carbon α to the carboxylate is sec-buytl substituted.

DETAILED DESCRIPTION OF THE INVENTION

The invention relates to compounds as shown in Formula I.

(Formula I)

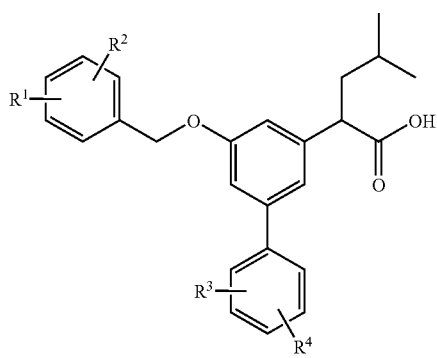

wherein:
R¹ is F, Cl, or CF₃;
R² is F, Cl, or CF₃;
R³is F, Cl, or CF₃
R⁴ is H, F, Cl, or CF₃;

and solvates, hydrates, esters, and pharmaceutically acceptable salts thereof.

In an embodiment of the invention:
R¹ is F;
R² is F, Cl, or CF₃;
R is CF₃;
R⁴ is H, F, Cl, or CF₃;

and solvates, hydrates, esters, and pharmaceutically acceptable salts thereof.

Another embodiment of the invention is a compound selected from the group consisting of:
(R)-2-[5-(3,5-Difluoro-benzyloxy)-4'-trifluoromethyl-biphenyl-3-yl]-4-methyl-pentanoic acid,
(S)-2-[5-(3,5-Difluoro-benzyloxy)-4'-trifluoromethyl-biphenyl-3-yl]-4-methyl-pentanoic acid,
2-[5-(4-Fluoro-2-trifluoromethyl-benzyloxy)-4'-trifluoromethyl-biphenyl-3-yl]-4-methyl-pentanoic acid,
2-[4'-Chloro-5-(3,5-difluoro-benzyloxy)-3'-trifluoromethyl-biphenyl-3-yl]-4-methyl-pentanoic acid, and solvates, hydrates, esters, and pharmaceutically acceptable salts thereof.

One skilled in the art will recognize that the compounds of Formula I may have one or more asymmetric carbon atoms in their structure. It is intended that the present invention include within its scope single enantiomer forms of the compounds, racemic mixtures, and mixtures of enantiomers in which an enantiomeric excess is present.

Some of the compounds of the inventions and/or salts or esters thereof will exist in different stereoisomeric forms. All of these forms are subjects of the invention.

Described below are exemplary salts of the compounds according to the invention which are included herein. The list of the different salts stated below is not meant to be complete and limiting.

Compounds according to the invention which contain one or more acidic groups can be used according to the invention, e.g. as their alkali metal salts, alkaline earth metal salts or ammonium salts. More precise examples of such salts include sodium salts, potassium salts, calcium salts, magnesium salts or salts with ammonia or organic amines such as, e.g. ethylamine, ethanolamine, triethanolamine or amino acids.

The term "pharmaceutically acceptable" means approved by a regulatory agency such as the EMEA (Europe) and/or the FDA (US) and/or any other national regulatory agency for use in animals, preferably in humans.

The respective salts of the compounds according to the invention can be obtained by customary methods which are known to the person skilled in the art, for example by contacting these with an organic or inorganic base in a solvent or dispersant, or by cation exchange with other salts.

Furthermore, the invention includes all salts of the compounds according to the invention which, owing to low physiological compatibility, are not directly suitable for use in pharmaceuticals but which can be used, for example, as intermediates for chemical reactions or for the preparation of pharmaceutically acceptable salts or which might be suitable for studying γ-secretase modulating activity of a compound according to the invention in any suitable manner, such as any suitable in vitro assay.

The present invention furthermore includes all solvates of the compounds according to the invention.

The present invention furthermore includes derivatives/prodrugs (including the salts thereof) of the compounds according to the invention which contain physiologically tolerable and cleavable groups and which are metabolized in animals, preferably mammals, most preferably humans into a compound according to the invention.

The present invention furthermore includes the metabolites of the compounds according to the invention.

The term "metabolites" refers to all molecules derived from any of the compounds according to the invention in a cell or organism, preferably mammal.

Preferably the term "metabolites" relates to molecules which differ from any molecule which is present in any such cell or organism under physiological conditions.

The structure of the metabolites of the compounds according to the invention will be obvious to any person skilled in the art, using the various appropriate methods.

The compounds according to general formula (I) can be prepared according to methods published in the literature or by analogous methods.

Depending on the circumstances of the individual case, in order to avoid side reactions during the synthesis of a compound of the general Formula (I), it can be necessary or advantageous to temporarily block functional groups by introducing protective groups and to deprotect them in a later stage of the synthesis, or to introduce functional groups in the form of precursor groups and at a later stage to convert them into the desired functional groups. Suitable synthetic strategies, protective groups and precursor groups are known to the person skilled in the art.

If desired, the compounds of the formula (I) can be purified by customary purification procedures, for example by recrystallization or chromatography. The starting materials for the preparation of the compounds of the formula (I) are commercially available or can be prepared according to or analogously to literature procedures.

These can serve as a basis for the preparation of the other compounds according to the invention by several methods well known to the person skilled in the art.

The invention also relates to a compound of the invention for use as a medicament. The compounds are as defined above, furthermore with respect to the medicament the embodiments as described below with respect to the use of the invention, e.g. formulation, application and combination, also apply to this aspect of the invention.

In particular the compounds according to the invention are suitable for the treatment of Alzheimer's disease.

Details relating to said use are further disclosed below.

The compounds can be used for modulation of γ-secretase activity.

As used herein, the term "modulation of γ-secretase activity" refers to an effect on the processing of APP by the γ-secretase-complex. Preferably it refers to an effect in which the overall rate of processing of APP remains essentially as without the application of said compounds, but in which the relative quantities of the processed products are changed, more preferably in such a way that the amount of the Aβ42-peptide produced is reduced. For example a different Abeta species can be produced (e.g. Abeta-38 or other Abeta peptide species of shorter amino acid sequence instead of Abeta-42) or the relative quantities of the products are different (e.g. the ratio of Abeta-40 to Abeta-42 is changed, preferably increased).

Gamma secretase activity can e.g. be measured by determining APP processing, e.g. by determining the levels of Abeta peptide species produced, most importantly levels of Abeta-42 (see Example section, infra).

It has been previously shown that the γ-secretase complex is also involved in the processing of the Notch-protein. Notch is a signaling protein which plays a crucial role in developmental processes (e.g. reviewed in Schweisguth F (2004) Curr. Biol. 14, R129).

With respect to the use of said compounds for the modulation of γ-secretase activity in therapy, it seems particularly advantageous not to interfere with the Notch-processing activity of the γ-secretase activity in order to avoid putative undesired side-effects.

Thus, compounds are preferred which do not show an effect on the Notch-processing activity of the γ-secretase-complex.

Within the meaning of the invention, "effect on the Notch processing activity" includes both an inhibition or an activation of the Notch-processing activity by a certain factor.

A compound is defined as not having an effect on the Notch processing activity, if said factor is smaller than 20, preferably smaller than 10, more preferably smaller than 5, most preferably smaller than 2 in the respective assay as described in Shimizu et al (2000) Mol. Cell. Biol, 20: 6913 at a concentration of 30 μM.

Such a γ-secretase modulation can be carried out, e.g. in animals such as mammals. Exemplary mammals are mice, rats, guinea pigs, monkeys, dogs, cats. The modulation can also be carried out in humans. In a particular embodiment of the invention, said modulation is performed in vitro or in cell culture. As known to the person skilled in the art, several in vitro and cell culture assays are available.

Exemplary assays useful for measuring the production of C-terminal APP fragments in cell lines or transgenic animals by Western blot analysis include but are not limited to those described in Yan et al., 1999, Nature 402, 533-537.

An example of an in vitro γ-secretase assay is described in WO-03/008635. In this assay a suitable peptide substrate is contacted with a γ-secretase preparation and the ability to cleave the substrate is measured.

Concentrations of the various products of the γ-secretase cleavage (the Aβ-peptides) can be determined by various methods known to a person skilled in the art. Examples for such methods include determination of the peptides by mass-spectrometry or detection by antibodies.

Exemplary assays useful for the characterization of the profile of soluble Aβ peptides in cultured cell media and biological fluids include but are not limited to those described by Wang et al., 1996, J. Biol. Chem. 271, 31894-31902. In this assay a combination of immunoprecipitation of Abeta-peptides with specific antibodies and detection and quantification of the peptide species with matrix-assisted laser desorption ionization time-of-flight mass spectrometry is used.

Exemplary assays useful for measuring the production of Abeta-40 and Abeta-42 peptides by ELISA include but are not limited to those described in Vassar et al, 1999, Science 286, 735-741. Further information is disclosed for example in N. Ida et al. (1996) J. Biol. Chem. 271, 22908, and M. Jensen et al. (2000) Mol. Med. 6, 291. Suitable antibodies are available for example from The Genetics Company, Inc., Switzerland. Antibody-based kits are also available from Innogenetics, Belgium.

Cells which can be employed in such assays include cells which endogenously express the γ-secretase complex and transfected cells which transiently or stably express some or all interactors of the γ-secretase complex. Numerous available cell lines suitable for such assays are known to the skilled person. Cells and cell lines of neuronal or glial origin are particularly suitable. Furthermore, cells and tissues of the brain as well as homogenates and membrane preparations thereof may be used (Xia et al., 1998, Biochemistry 37, 16465-16471).

Such assays might be carried out for example to study the effect of the compounds according to the invention in different experimental conditions and configurations.

Furthermore, such assays might be carried out as part of functional studies on the γ-secretase complex.

For example, either one or more interactors (either in their wild-type form or carrying certain mutations and/or modifications) of the γ-secretase complex of an animal, preferably a mammal, more preferably humans, might be expressed in certain cell lines and the effect of the compounds according to the invention might be studied.

Mutated forms of the interactor(s) used can either be mutated forms which have been described in certain animals, preferably mammals, more preferably humans or mutated forms which have not previously been described in said animals.

Modifications of the interactors of the γ-secretase complex include both any physiological modification of said interactors and other modifications which have been described as modifications of proteins in a biological system.

Examples of such modifications include, but are not limited to, glycosylation, phosphorylation, prenylation, myristylation and farnesylation.

Furthermore, the compounds according to the invention can be used for the preparation of a medicament for the modulation of γ-secretase activity.

The invention further relates to the use of said compounds for the preparation of a medicament for the modulation of γ-secretase activity.

The activity of the γ-secretase can be modulated in different ways, i.e. resulting in different profiles of the various Aβ-peptides.

Uses of a compound for the modulation of γ-secretase activity resulting in a decrease in the relative amount of Aβ42-peptides produced are preferred.

Respective dosages, routes of administration, formulations etc are disclosed further below.

The invention further relates to the use of the compounds according to the invention for the treatment of a disease associated with an elevated level of Aβ42-production. The disease with elevated levels of Abeta peptide production and deposition in the brain is typically Alzheimer's disease (AD), cerebral amyloid angiopathy, multi-infarct dementia, dementia pugilistica or Down syndrome, preferably AD.

As used herein, the term "treatment" is intended to refer to all processes, wherein there may be a slowing, interrupting, arresting, or stopping of the progression of a disease, but does not necessarily indicate a total elimination of all symptoms.

As used herein, the term "elevated level of Aβ42-production" refers to a condition in which the rate of production of Aβ42-peptide is increased due to an overall increase in the processing of APP or, preferably, it refers to a condition in which the production of the Aβ42 peptide is increased due to a modification of the APP-processing profile in comparison to the wild-type APP and non-pathological situation.

As outlined above, such an elevated Aβ42-level is a hallmark of patients developing or suffering from Alzheimer's disease.

One advantage of the compounds or a part of the compounds of the present invention may lie in their enhanced CNS-penetration.

Furthermore the invention relates to a pharmaceutical composition comprising a compound according to the invention in a mixture with an inert carrier.

In a preferred embodiment, the invention relates to a pharmaceutical composition comprising a compound according to the invention in a mixture with an inert carrier, where said inert carrier is a pharmaceutical carrier.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water is a preferred carrier when the pharmaceutical composition is administered orally. Saline and aqueous dextrose are preferred carriers when the pharmaceutical composition is administered intravenously. Saline solutions and aqueous dextrose and glycerol solutions are preferably employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

The compounds according to the invention and their pharmaceutically acceptable salts, optionally in combination with other pharmaceutically active compounds are suitable to treat or prevent Alzheimer's disease or the symptoms thereof. Such additional compounds include cognition-enhancing drugs such as acetylcholinesterase inhibitors (e.g. Donepezil, Tacrine, Galantamine, Rivastigmin), NMDA antagonists (e.g. Memantine) PDE4 inhibitors (e.g. Ariflo) or any other drug known to a person skilled in the art suitable to treat or prevent Alzheimer's disease. Such compounds also include cholesterol-lowering drugs such as statins (e.g. simvastatin). These compounds can be administered to animals, preferably to mammals, and in particular humans, as pharmaceuticals by themselves, in mixtures with one anther or in the form of pharmaceutical preparations.

Various delivery systems are known and can be used to administer a compound of the invention for the treatment of Alzheimer's disease or for the modulation of the γ-secretase activity, e.g. encapsulation in liposomes, microparticles, and microcapsules:

If not delivered directly to the central nervous system, preferably the brain, it is advantageous to select and/or modify methods of administration in such a way as to allow the pharmaceutical compound to cross the blood-brain barrier.

Methods of introduction include, but are not limited to, intradermal, intramuscular, intraperitoneal, intravenous, subcutaneous, intranasal, epidural, and oral routes.

The compounds may be administered by any convenient route, for example by infusion, by bolus injection, by absorption through epithelial or mucocutaneous linings and may be administered together with other biologically active agents.

Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g. by use of an inhaler or nebulizer, and formulation with an aerosolizing agent.

In another embodiment, the compound can be delivered in a vesicle, in particular a liposome (Langer (1990) Science 249, 1527.

In yet another embodiment, the compound can be delivered via a controlled release system. In one embodiment, a pump may be used (Sefton (1987) CRC Crit. Ref. Biomed. Eng. 14, 201; Buchwald et al. (1980) Surgery 88, 507; Saudek et al. (1989) N. Engl. J. Med. 321, 574). In another embodiment, polymeric materials can be used (Ranger and Peppas (1983) Macromol. Sci. Rev. Macromol. Chem. 23, 61; Levy et al. (1985) Science 228, 190; During et al. (1989) Ann. Neurol. 25, 351; Howard et al. (1989) J. Neurosurg. 71, 858). In yet another embodiment, a controlled release system can be placed in proximity of the therapeutic target, i.e., the brain, thus requiring only a fraction of the systemic dose (e.g. Goodson, 1984, In: Medical Applications of Controlled Release, supra, Vol. 2, 115). Other controlled release systems are discussed in the review by Langer (1990, Science 249, 1527).

In order to select an appropriate way of administration, the person skilled in the art will also consider routes of administration which have been selected for other known Anti-Alzheimer-drugs.

For example, Aricept/Donepezil and Cognex/Tacrine (all acetylcholinesterase-inhibitors) are being taken orally, Axura/Memantine (an NMDA-receptor antagonist) has been launched both as tablets/liquid and as an i.v.-solution.

Furthermore, the skilled person in the art will take into account the available data with respect to routes of administration of members of the NSAID-family in clinical trials and other studies investigating their effect on Alzheimer's disease.

In order to select the appropriate dosage, the person skilled in the art will choose a dosage which has been shown to be not toxic in preclinical and/or clinical studies and which can be in accordance with the values given beforehand, or which may deviate from these.

The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20-500 micrograms of active compound per kilogram body weight. Suitable dosage ranges for intranasal administration are generally about 0.01 mg/kg body weight to 1 mg/kg body weight. Effective doses may be extrapolated from dose-response curves derived from in vitro or animal model test systems.

An exemplary animal model is the transgenic mouse strain "Tg2576" containing an APP695-form with the double mutation KM670/671NL. For reference see e.g. patent U.S. Pat. No. 5,877,399 and Hsiao et al. (1996) Science 274, 99 and also Kawarabayahsi T (2001) J. Neurosci. 21, 372; Frautschy et al. (1998) Am. J. Pathol. 152, 307; Irizarry et al. (1997) J. Neuropathol. Exp. Neurol. 56, 965; Lehman et al. (2003) Neurobiol. Aging 24, 645.

Substantial data from several studies are available to the skilled person in the art, which are instructive to the skilled person to select the appropriate dosage for the chosen therapeutic regimen.

Numerous studies have been published in which the effects of molecules on the γ-secretase activity are described. Exemplary studies are Lim et al. (2001) Neurobiol. Aging 22, 983; Lim et al. (2000) J Neurosci. 20, 5709; Weggen et al. (2001) Nature 414, 212; Eriksen et al. (2003) J Clin Invest. 112, 440; Yan et al. (2003) J Neurosci. 23, 7504.

General Synthesis Description

The following general description is for illustrative purposes only and is in no way meant to limit the invention.

The compound of Formula I wherein $R^1$, $R^2$, $R^3$, and $R^4$ are defined as in Formula I, may be obtained by hydrolysis of ester II under standard acidic or basic hydrolysis conditions, including reaction with NaOH, at room temperature, for several hours, in an appropriate solvent mixture, such as water, tetrahydrofuran (THF), and methanol.

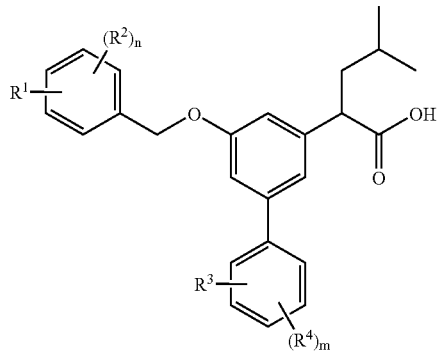

I

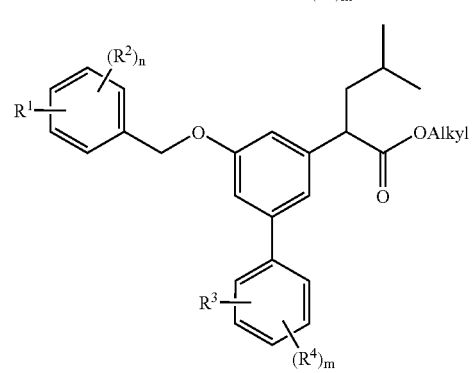

II

Compound II, wherein alkyl includes methyl and ethyl, may be obtained by alkylation of compound III with benzyl bromides, benzyl chlorides, benzyl tosylates, or benzyl mesylates under typical benzylation conditions, e.g. in DMF or THF in the presence of base, such as. potassium carbonate or cesium carbonate with temperature rages from 25-120 degrees C. Compound II may also be obtained by reaction of compound III with a benzyl alcohol under Mitsnobu conditions, e.g. in THF or toluene in the presence of diethyl azodicarboxylate and triphenylphosphine.

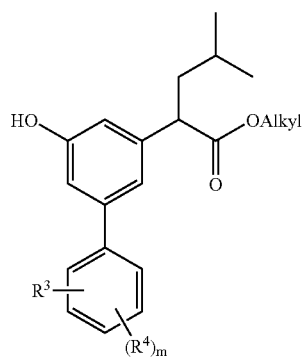

III

Compound III may be prepared by debenzylation of compound IV by hydrogenation in alcohol, e.g. MeOH or EtOH in the presence of Pd—C. Debenzylation can also be achieved with other methods, such as $BBr_3$ in DCM, NaCN in DMSO/ 120-200° C. or LiCN in DMF/120-200° C.

IV

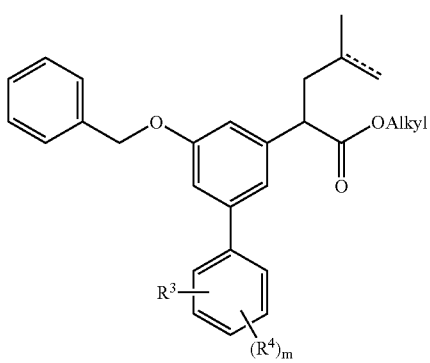

Compound IV may be prepared from alkylation of compound V with either sec-butyl bromide or sec-butenyl bromide. Treatment of compound V in THF or another aprotic solvent with a base, e.g. lithium bis(trismethylsilyl)amide, sodium bis(trismethylsilyl)amide, or lithium diisopropylamide at −78° C., followed by the addition of sec-butyl bromide or sec-butenyl bromide yields alkylated compound IV.

V

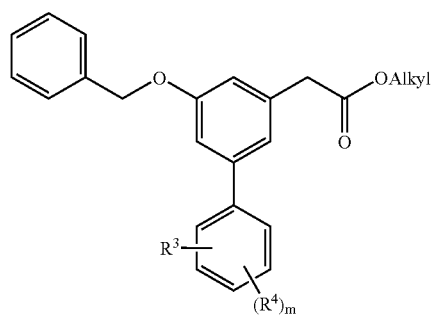

Compound V may be prepared from compound VI through a coupling reaction with an arylboronic acid under Suzuki conditions of aqueous sodium carbonate in DME in the presence of Pd(PPh$_3$)$_4$.

VI

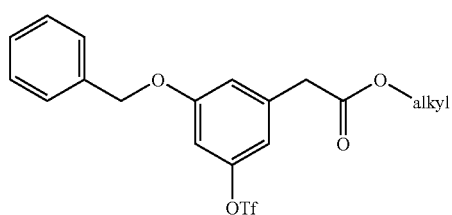

Intermediate compound VI may be prepared from compound VII with trifluoromethanesulfonic anhydride in DCM in the presence of one equivalent of pyridine at 0° C.

VII

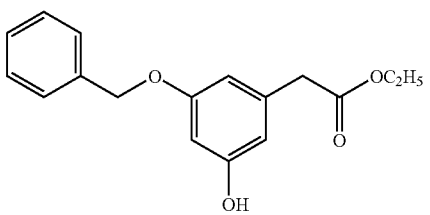

Intermediate phenolic ester VII can be prepared from mono-debenzylation of compound VIII. Selective mono-debenzylation of compound VIII can be achieved by treatment with 1.1 equivalents of base, e.g. sodium hydroxide or potassium hydroxide, in ethanol or methanol solution in the presence of Pd—C catalyst under hydrogen atmosphere (<60 psi) in a Parr shaker. The reaction is allowed to proceed until one equivalent of hydrogen is consumed.

VIII

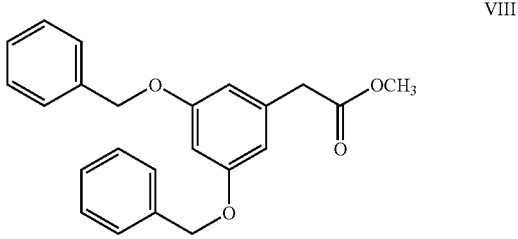

Intermediate VIII can be easily prepared from reaction of 3,5-dihydroxyphenyl acetic acid methyl ester (commercially available) with benzyl bromide and potassium carbonate in DMF at room temperature.

Compound I has a chiral center α to the carboxylic group, and can exist as one of two enantiomers (or a mixture thereof, wherein an enantiomeric excess may or may not be present). The enantiomers Ia (R enantiomer) and Ib (S enantiomer) are shown. The pure enantiomers Ia and Ib be obtained by chiral separation using a chiral column. The enantiomers Ia and Ib may also be separated by resolutions through forming chiral amine salts by fractional recrystallizations. The enantiomers Ia and Ib also may be obtained from kinetic resolution of the racemate of corresponding esters using lipase enzymes, e.g. AmanoAk, Amano lipase PS, Amano lipaseA, Amano lipase M, Amano lipase F-15 Amano lipase G (from Biocatalytics Inc) in aqueous organic solvents, e.g. aqueous DMF, DMSO, t-butyl-ethyl ether or triton X-100 aqueous solutions.

Both enantiomers of compound I may be prepared from chiral syntheses. Compounds Ia and Ib may be obtained from the removal of the chiral auxiliary groups from compounds IXa and IXb respectively with lithium hydroxide in aqueous THF in the presence of hydrogen peroxide.

Ia

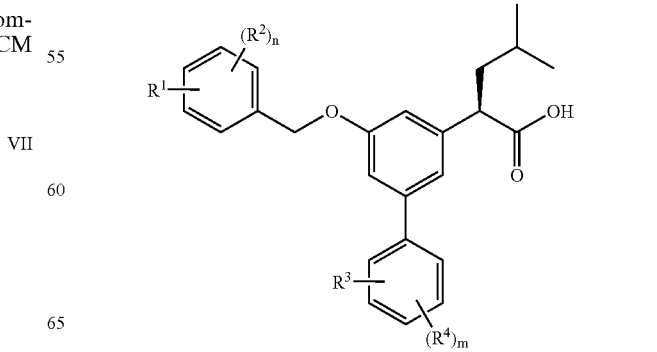

-continued

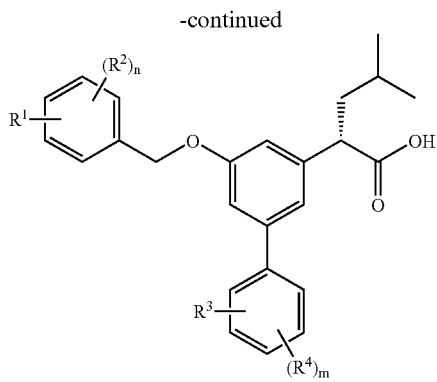
Ib

Compounds IXa and IXb may be obtained by coupling compounds Xa and Xb with benzyl bromides, chlorides or tosylates or mesylates under typical base conditions, e.g. in DMF or THF in the presence of base. e.g. potassium carbonate or cesium carbonate temperature rages from 25-120 degrees C. Compounds IXa and IXb may also be obtained by coupling reaction of compounds Xa and Xb with benzyl alcohols under the Mitsnobu conditions, e.g. in THF or toluene in the presence of diethyl azodicarboxylate and triphenylphosphine.

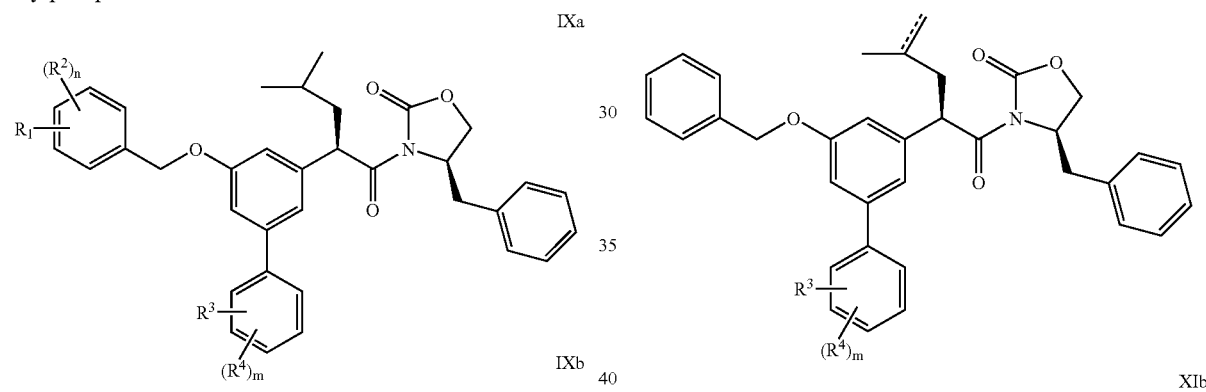

Compounds Xa and Xb may be prepared from debenzylation of compounds XIa and XIb respectively by hydrogenation in an alcohol solvent, e.g. MeOH or EtOH, in the presence of Pd—C.

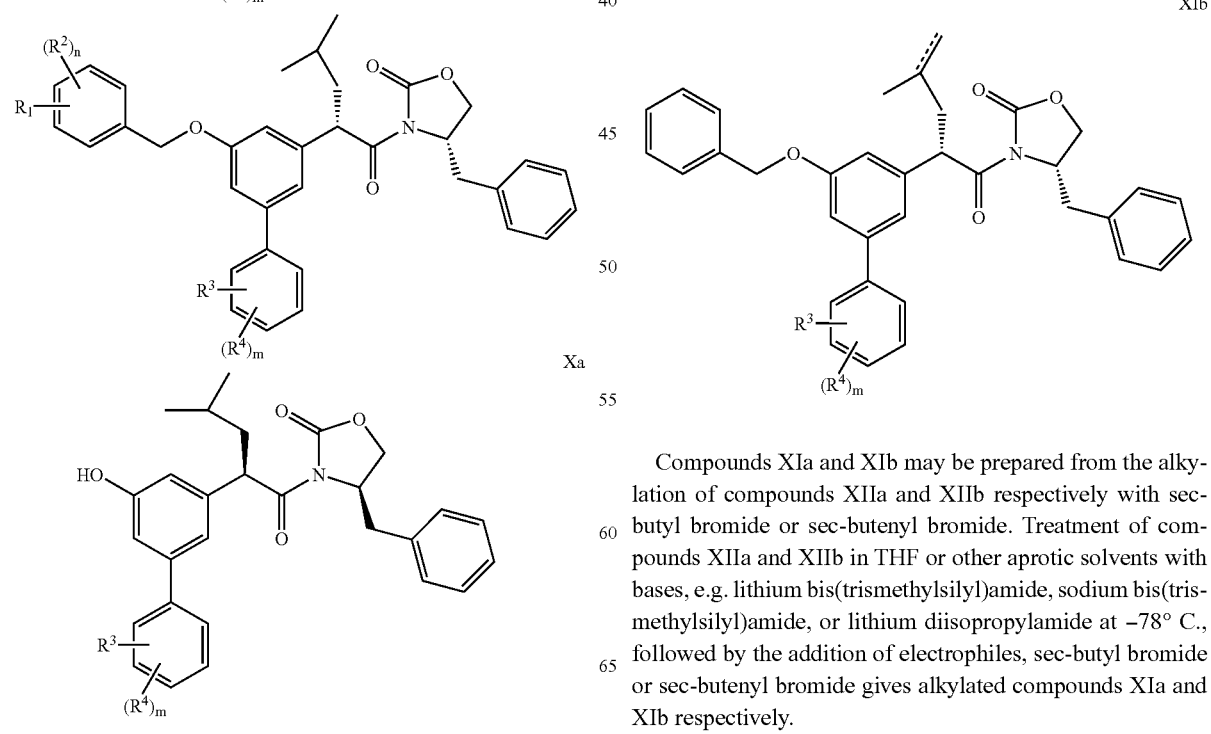

Compounds XIa and XIb may be prepared from the alkylation of compounds XIIa and XIIb respectively with sec-butyl bromide or sec-butenyl bromide. Treatment of compounds XIIa and XIIb in THF or other aprotic solvents with bases, e.g. lithium bis(trismethylsilyl)amide, sodium bis(trismethylsilyl)amide, or lithium diisopropylamide at −78° C., followed by the addition of electrophiles, sec-butyl bromide or sec-butenyl bromide gives alkylated compounds XIa and XIb respectively.

XIIa

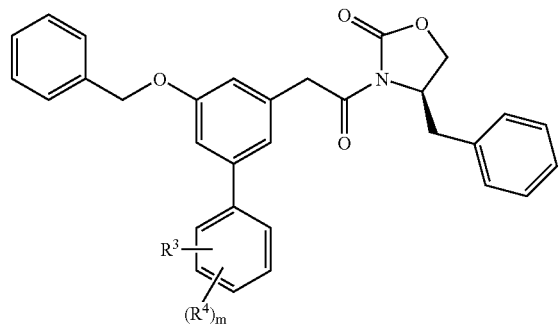

XIIb

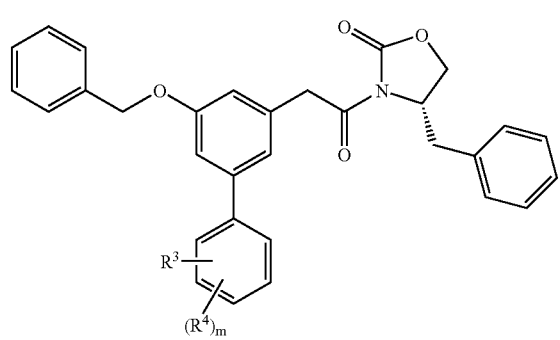

Compounds XIIa and XIIb may be prepared from the common intermediate XIII by coupling with either R-isomer of 4-benzyl-oxazolidin-one XIVa or S-isomer of 4-benzyl-oxazolidin-one XIVb by Evans's procedures. Intermediate XIII may be reacted with pivaloyl chloride, oxalyl chloride or isopropyl chloroformate in THF in the presence of a base, e.g. triethylamine or N-methylmorpholine, to mixed anhydrides or acid chlorides which then were reacted with the lithium salt of XIVa or XIVb in THF. Other chiral auxiliary groups may also be used in the chiral syntheses, e.g. pseudoephedrine via the A. G. Myers conditions (J. Am. Chem. Soc. 1994, 116, 9361-9362). Treatment of either of enantiomer of pseudoephedrine with carboxylic acicid chlorides or anhydrides leads to amide derivative XV. The amides are treated with a strong base, e.g. lithium diisopropyl amide in the presence of lithium chloride, followed by the addition of an alkylating agent to yield the corresponding alkylated products. The chiral auxiliary group then may then be removed in acid hydrolysis to give the chiral target compounds.

XIII

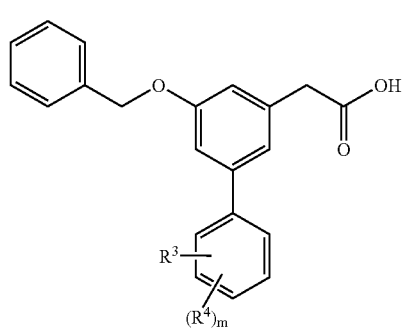

XIVa

XIVb

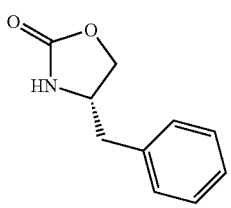

XV

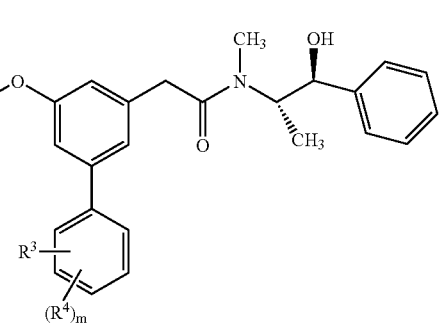

Intermediate compound XIII may be obtained from ester hydrolysis of compound V with base in aqueous alcohol solution, e.g. LiOH or NaOH in aqueous methanol solution.

Synthetic Procedures

All reactions were carried out under inert atmosphere unless otherwise stated. NMR spectra were obtained on a Bruker dpx400. LCMS was carried out on an Agilent 1100 using a ZORBAX® SB-C18, 4.6×75 mm, 3.5 micron column for method A. Column flow was 1 ml/min and solvents used were water and acetonitrile (0.1% TFA) with an injection volume of 10 ul. Wavelengths were 254 and 210 nm. The chiral purity analyses were performed by chiral columns Abbreviations

| | |
|---|---|
| Ac | Acetyl |
| d | Doublet |
| DCM | Dichloromethane |
| DME | 1,2-dimethoxyethane |
| DMF | N,N-dimethylformamide |
| DMSO | Dimethyl sulfoxide |
| e.e. | enantiomeric excess |
| Eq | Equivalents |
| Et | Ethyl |
| EtOAc | ethyl acetate |
| g | Gram |
| h | Hour |
| ISCO | Telydyne ISCO Chromatography |
| HPLC | high pressure liquid chromatography |
| $K_2CO_3$ | Potassium carbonate |
| l | Litre |
| LCMS | liquid chromatography - mass spectrometry |
| LDA | lithium diisopropylamide |
| M | Molar |
| m | Multiplet |

| | |
|---|---|
| Me | Methyl |
| min | Minute |
| mol | Mole |
| NMR | nuclear magnetic resonance |
| q | Quartet |
| RT | Retention time |
| s | Singlet |
| sat | Saturated |
| t | Triplet |
| TFA | Trifluoroacetic acid |
| THF | Tetrahydrofuran |

EXAMPLES

Example 1

(R) 2-[5-(3,5-Difluoro-benzyloxy)-4'-trifluoromethyl-biphenyl-3-yl]-4-methyl-pentanoic acid

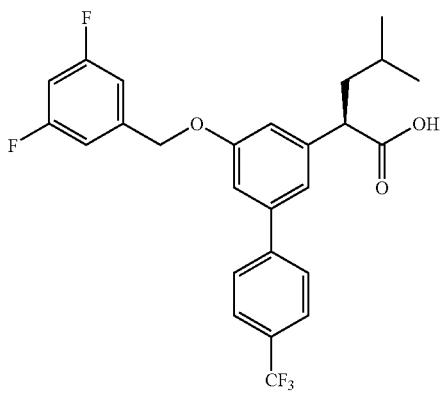

Racemic Synthesis and Chiral Separation a) (3,5-Bis-benzyloxy-phenyl)-acetic acid methyl ester

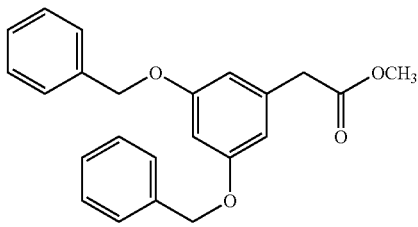

A mixture of (3,5-dihydroxy-phenyl)-acetic acid methyl ester (from Aldrich, 70 g, 0.385 mole), benzylbromide (137 mL, 1.16 mole), potassium carbonate (160 g, 1.16 mole) and DMF (1.5 L) under $N_2$ was mechanically stirred at room temperature overnight. The resulting reaction mixture was poured into a mixture of 1.5 L of ice-water with stirring. The precipitate was obtained by filtration and washed with heptane successively to remove benzyl bromide to give the title compounds (123.7 g) as a brown solid which was air dried for the next reaction. $^1$H-NMR(CDCl$_3$): δ 3.60 (s, 2H), 3.71(s, 3H), 5.05 (s, 4H), 6.60 (s, 3H), 7.35-7.50 (m, 10H); Calcd for C23H22O4 (M+H) 363.15, Found 363.

b) 3-Benzyloxy-5-hydroxy-phenyl)-acetic acid ethyl ester

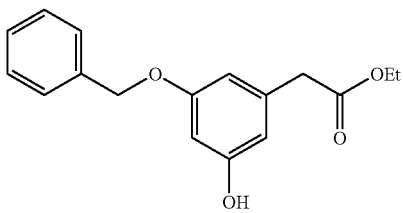

A solution of 50 grams (1.38 moles) of 3,5-Bis-benzyloxy-phenyl)-acetic acid methyl ester and NaOH (6.6 g, 1.65 moles) in 1 L of EtOH in the presence of 10% of Pd—C was hydrogenated in a Parr shaker until one equivalent of hydrogen was consumed. The mixture was acidified with concentrated HCl and then the catalyst and solvent were removed to give an oil residue. The crude product was purified by ISCO silica gel column chromatography (ISCO) using EtOAC-heptane as eluents (gradient from 10% to 75% of EtOAc) to give 25 grams (65% yield) the title compound (1b). $^1$H-NMR(CDCl$_3$): δ 1.15-1.20 (t, 3H), 3.4-(s,2H), 4.05-4.1 (q, 2H),4.9 (s, 2H), 5.5(s, 1H), 6.4(s, 2H), 6.5(s, 1H), 7.207.35(m, 5H); Calcd for C17H18O4 (M+H) 287.3, Found 287.

c) (3-Benzyloxy-5-trifluoromethanesulfonyloxy-phenyl)-acetic acid ethyl ester

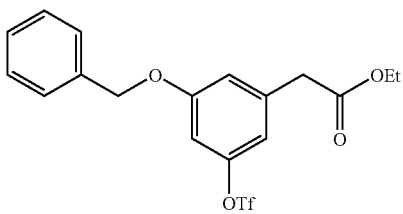

To a solution of 3-(benzyloxy-5-hydroxy-phenyl)-acetic acid ethyl ester (74.4 g, 0.26 mol) in dichloromethane (700 mL) was added pyridine (62.5 mL, 0.78 mol). The mixture was cooled to 0° C. To this cold solution was added trifluoromethanesulfonic anhydride (65.6 mL, 0.39 mol), over 1.5 h, maintaining the internal temperature below 5° C. and stirred for an additional 0.5 h at 0° C. This reaction mixture was poured to a mixture of 1 N HCl (420 mL), and wet-ice (105 g) and stirred for 0.5 h. The aqueous layer was extracted with dichloromethane (2×100 mL). Combined fractions were washed with water (2×100 mL), saturated aqueous NaHCO$_3$ solution (2×100 mL), and brine (2×100 mL). The organics were dried (MgSO$_4$) and concentrated in vacuo to receive a reddish liquid (108 g) which was carried on to the next step without further purification. Calcd for C18H17F3O6S (M+H) 419.07, Found 419.1.

d) (5-Benzyloxy-4'-trifluoromethyl-biphenyl-3-yl)-acetic acid ethyl ester

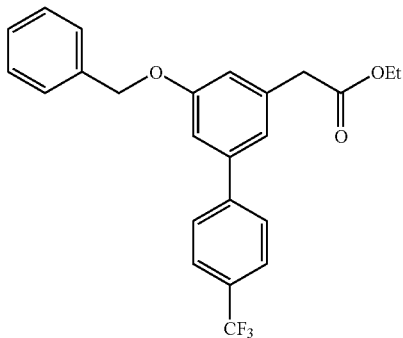

A mixture of (3-benzyloxy-5-trifluoromethanesulfonyloxy-phenyl)-acetic acid ethyl ester (108 g, 0.26 mol), 4-(trifluoromethyl)phenylboronic acid (55.6 g, 0.29 mol), 1,2-dimethoxyethane (1.1 L) and aqueous $Na_2CO_3$ (2 M, 129 mL, 0.6 mol) was mechanically stirred while purging $N_2$ at room temperature for 10 min. To this system was added $Pd(Ph_3)_4$ (480 mg, 0.42 mmol) and heated to reflux (95° C.) for 2.5 h. The red-brown mixture was diluted with EtOAc (0.5 L) and washed with saturated aqueous $NaHCO_3$ solution (3×200 mL) and brine (2×200 mL). The organic fraction was dried ($Na_2SO_4$) and concentrated in vacuo. The crude mixture was purified by ISCO column chromatography to obtain (5-benzyloxy-4'-trifluoromethyl-biphenyl-3-yl)-acetic acid ethyl ester (107 g, 100%).

$^1$H-NMR (CDCl$_3$): δ 1.26 (t, 3H), 3.66 (s, 2H), 4.17 (q, 2H), 5.12 (s, 2H), 6.99 (s, 1H), 7.12 (s, 2H), 7.34-7.49 (m, 5H), 7.67 (s, 4H); Calcd for C24H21F3O3 (M+H) 415.14, Found 415.2.

e) 2-(5-Benzyloxy-4'-trifluoromethyl-biphenyl-3-yl)-4-methyl-pent-4-enoic acid ethyl ester

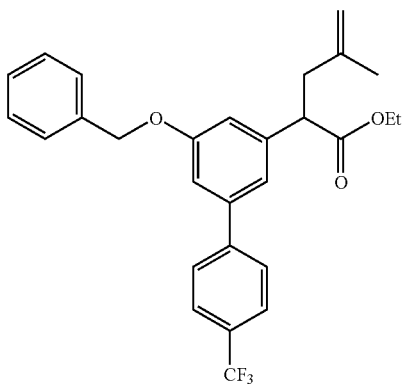

To a solution of compound 1d (4.9 g, 11.8 mmole) in THF (50 mL) at −78° C. was added Li[N(SiMe$_3$)$_2$] (1N in THF, 14.2 mL, 14.2mmol) dropwise. The reaction mixture was stirred for 1 h at −78° C. and then 3-bromo-2-methyl-propene (1.25 mL, 12.4mmole) was added dropwise. The solution was slowly warmed up to −35° C. and stirred at −35° C. for 0.5 h. The reaction was quenched with NH$_4$Cl saturated solution and extracted with EtOAc. The organic extracts was dried (Na$_2$SO$_4$), concentrated and purified by column chromatography give compound 1e (5.1 g, 92%) as a clear oil; 1H NMR (400 MHz, CHLOROFORM-D) δ ppm 1.19-1.29 (m, 3 H), 1.74 (s, 3 H), 2.47 (m, 1 H), 2.85 (m, 1 H), 3.83 (m, 1 H), 4.11 (m, 2 H), 4.72 (s, 1 H), 4.77 (s, 1 H), 5.12 (s, 2 H), 7.03 (s, 1 H), 7.10 (s, 1 H), 7.15 (s, 1 H), 7.35-7.48 (m, 5 H), 7.67 (s, 4 H); Calcd for C28H27F3O3 (M+H) 469.19, Found 469.

f) 2-(5-Hydroxy-4'-trifluoromethyl-biphenyl-3-yl)-4-methyl-pentanoic acid ethyl ester

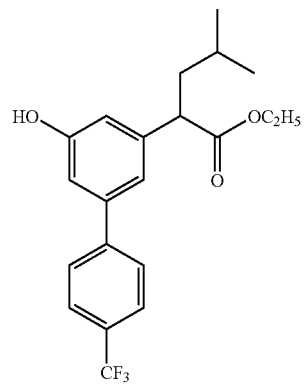

A mixture of compound 1e (5.1 g, 10.9 mmole), 10% Pd/C (500 mg) in EtOH (50 mL) was hydrogenated under H$_2$ (40 psi) in par-shaker for 20 h. The resulting reaction mixture was filtered through celite and the filtrate was concentrated to give compound 1f (4.2 g, 100%) as a clear oil; 1H NMR (300 MHz, CHLOROFORM-D) δ ppm 0.92 (d, J=6.6 Hz, 6 H), 1.25 (m, 3 H), 1.49-1.61 (m, 1 H), 1.65-1.70 (m, 1 H), 1.95-2.05 (m, 1 H), 3.67 (t, J=7.7 Hz, 1 H), 4.10-4.29 (m, 2 H), 6.91 (s, 1 H), 6.97 (t, J=2.0 Hz, 1 H), 7.08 (s, 1 H), 7.65 (s, 4 H); Calcd for C21H23F3O3 (M+H) 381.16, Found 381.

g) 2-[5-(3,5-Difluoro-benzyloxy)-4'-trifluoromethyl-biphenyl-3-yl]-4-methyl-pentanoic acid To a solution of compound 1f (4 g, 10 mmole) in DMF was added cesium carbonate (g, 15 mmoe) and then 3, 5 difluorobenzylbromide. The resulting solution was stirred at rt for 18 h and then was quenched with water. The aqueous solution was extracted with EtOAc. The organic layer was washed, dried and evaporated to give a residue (5 g). The crude was then in 1N KOH in MeOH (3eq.) at rt overnight. The solution was acidified with con. HCl and then was extracted with EtOAc. The organic layer was then washed with water, dried over Na2SO4, then evaporated on a rotary evaporator to give a crude product. The crude was triturated heptane to afford 4.3 g (91% yield) of (R) and (S) product.

The racemic mixture was chirally separated by with Chiralpak AD column using methanol and acetonitril containing 0.1% of formic acid as an eluent to obtain (R) enantiomer, Compound 1, and (S) enantiomer, Compound 2, respectively.

The (R) enantiomer was found to has rotation −27.29 degrees in MeOH and the (S) enantiomer has rotation +25.2 degrees in MeOH. The absolute stereochemistry centers were assigned by correlation with the synthetic materials described below.

Chiral Synthesis of (R)-2-[5-(3,5-Difluoro-benzyloxy)-4'-trifluoromethyl-biphenyl-3-yl]-4-methyl-pentanoic acid h) 5-Benzyloxy-4'-trifluoromethyl-biphenyl-3-yl)-acetic acid

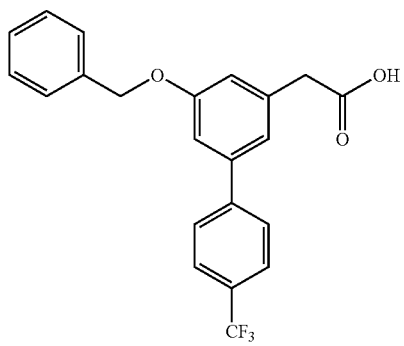

To a solution of (5-benzyloxy-4'-trifluoromethyl-biphenyl-3-yl)-acetic acid ethyl ester (120 g, 0.29 mol) in THF (1.2 L) was added water (240 mL), LiOH.H$_2$O (16 g, 0.32 mol) and the resulting mixture was stirred at room temperature for 16 h. The solution was filtered and concentrated in vacuo to remove THF. The resulting thick liquid was acidified to pH 2 by adding 2N aqueous HCl solution and the white suspension was mechanically stirred for 1 h at room temperature. The wet white product was recovered after filtration and dissolved in EtOAc (500 mL). The organic layer was separated from water, dried (MgSO$_4$) and concentrated in vacuo to obtain (5-benzyloxy-4'-trifluoromethyl-biphenyl-3-yl)-acetic acid (105 g, 94%).

$^1$H-NMR (d$_6$-DMSO): δ 3.64 (s, 2H), 5.18 (s, 2H), 7.02 (s, 1H), 7.24 (d, 2H), 7.34-7.50 (m, 5H), 7.81 (d, 2H), 7.89 (d, 2H), 12.25 (bs, 0.6H); Calcd for C22H17F3O3 (M+H) 387.11, Found 387.1.

i) 4-Benzyl-3-[2-(5-benzyloxy-4'-trifluoromethyl-biphenyl-3-yl)-acetyl]-oxazolidin-2-one

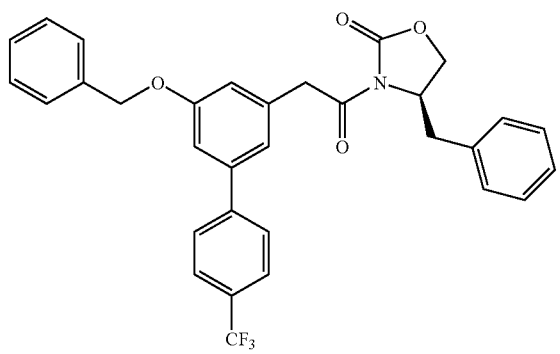

To a mechanically stirred solution of (5-benzyloxy-4'-trifluoromethyl-biphenyl-3-yl)-acetic acid (20 g, 52 mmol) in THF (104 mL) at −78° C. was added N-methyl morpholine (NMM) (6.3 mL, 57 mmol) and trimethylacetyl chloride (7.0 mL, 57 mmol) maintaining the internal temperature below −70° C. This mixture was stirred at −78° C. for 15 minutes and 0° C. at 1 h. The white solid was filtered off to receive the anhydride in the filtrate which was cooled back to −78° C. In a separate flask, to a solution of (R)-(+)-4-benzyl-2-oxazolidinone (9.6 g, 54.4 mmol) in THF (109 mL) at −78° C. was added nBuLi (1.6M in hexanes, 34 mL, 54.4 mol), drop-wise, maintaining the internal temperature below −70° C. and stirred at −78° C. for 45 min. This metalated chiral auxiliary was cannulated to the anhydride at −78° C. and warmed to 0° C. over 1.5 h. The resulting mixture was stirred further at 0° C. for 30 minute and quenched by adding excess saturated aqueous NH$_4$Cl solution. The solution was diluted with EtOAc (200 mL) and the organic phase was washed with saturated aqueous NaHCO$_3$ solution (3×100 mL) and brine (2×100 mL). The solution was dried over MgSO$_4$ and the solvent was removed in vacuo. The crude material was purified by ISCO silica gel column chromatography to yield 20.3 g (72%) of 4-benzyl-3-[2-(5-benzyloxy-4'-trifluoromethyl-biphenyl-3-yl)-acetyl]-oxazolidin-2-one as a white solid.

$^1$H-NMR (CDCl$_3$): δ 2.76 (dd, 1H), 3.26 (dd, 1H), 4.19 (m, 2H), 4.35 (q, 2H), 4.69 (m, 1H), 5.13 (s, 2H), 7.04-7.46 (m, 13H), 7.67 (s, 4H); Calcd for C32H26F3NO4 (M+H) 546.18, Found 546.3.

j) 4-Benzyl-3-[2-(5-benzyloxy-4'-trifluoromethyl-biphenyl-3-yl)-4-methyl-pent-4-enoyl]-oxazolidin-2-one

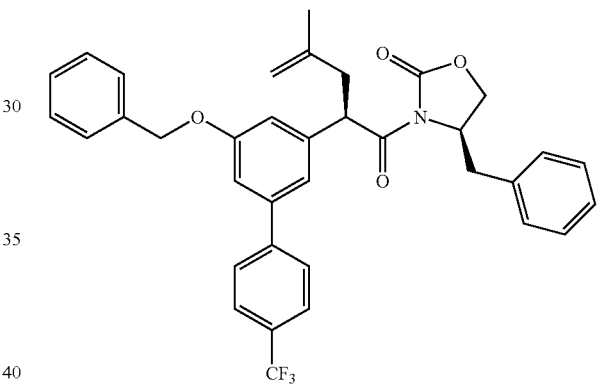

To a colorless solution of 4-benzyl-3-[2-(5-benzyloxy-4'-trifluoromethyl-biphenyl-3-yl)-acetyl]-oxazolidin-2-one (6.0 g, 11.00 mmol) in dry THF (22 ML) at −78° C. was added sodium hexamethyl disilazide (NaHMDS) (1 M in THF solution, 12.11 mL, 12.11 mmol), drop-wise, maintaining the internal temperature below −75° C. The resulting red solution was stirred at −78° C. for 30 minutes. To this was added 3-bromo-2-methyl propene (4.44 mL, 44 mmol) maintaining the temperature below −75° C. When the addition was at near completion, the reaction mixture turned green. At this point the dry-ice bath was quickly removed and replaced with water-ice bath and the addition was completed. The reaction mixture was stirred at 0° C. for an additional 30 min and quenched with saturated aqueous NH$_4$Cl solution. The system was diluted with EtOAC (100 mL) and the organic phase was washed with saturated aqueous NaHCO$_3$ solution (3×50 mL) and dried (MgSO$_4$). Solvent was removed in vacuo and the crude mixture was purified by ISCO silica gel column to yield 4-benzyl-3-[2-(5-benzyloxy-4'-trifluoromethyl-biphenyl-3-yl)-4-methyl-pent-4-enoyl]-oxazolidin-2-one (6.3 g, 95%)

$^1$H-NMR (CDCl$_3$): δ 1.80 (s, 3H), 2.46 (dd, 1H), 2.75 (dd, 1H), 3.05 (dd, 1H), 3.32 (dd, 1H), 4.08 (m, 2H), 4.59 (m, 1H), 4.80 (d, 2H), 5.13 (s, 2H), 5.48 (dd, 1H), 7.11 (d, 2H), 7.21-7.49 (m, 11H), 7.67 (s, 4H); Calcd for C36H32F3NO4 (M+H) 600.23, Found 600.3.

k) 4-Benzyl-3-[2-(5-hydroxy-4'-trifluoromethyl-biphenyl-3-yl)-4-methyl-pentanoyl]-oxazolidin-2-one

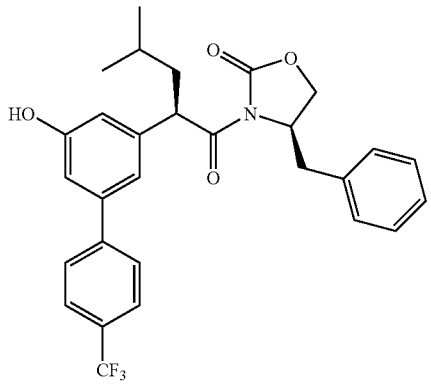

To a solution of 4-benzyl-3-[2-(5-benzyloxy-4'-trifluoromethyl-biphenyl-3-yl)-4-methyl-pent-4-enoyl]-oxazolidin-2-one (6.7 g, 11.2 mmol) in MeOH (150 mL) was added 10% Pd/C (670 mg, 10 w %). The black suspension was hydrogenated at 45-45 psi overnight. The mixture was filtered through celite and the solvent was remixed in vacuo to obtain relatively pure 4-benzyl-3-[2-(5-hydroxy-4'-trifluoromethyl-biphenyl-3-yl)-4-methyl-pentanoyl]-oxazolidin-2-one (5.4 g, 93%).

$^1$H-NMR (CDCl$_3$): δ 0.94 (d, 3H), 0.98 (d, 3H), 1.54 (m, 1H), 1.74 (m, 1H), 2.12 (m, 1H), 2.79 (dd, 1H), 3.36 (dd, 1H), 4.11 (m, 2H), 4.62 (m, 1H), 5.25 (t, 1H), 6.97 (m, 2H), 7.21-7.37 (m, 6H), 7.67 (s, 4H); Calcd for C29H28F3NO4 (M+H) 512.20, Found 512.3.

l) 4-Benzyl-3-{2-[5-(3,5-difluoro-benzyloxy)-4'-trifluoromethyl-biphenyl-3-yl]-4-methyl-pentanoyl}-oxazolidin-2-one

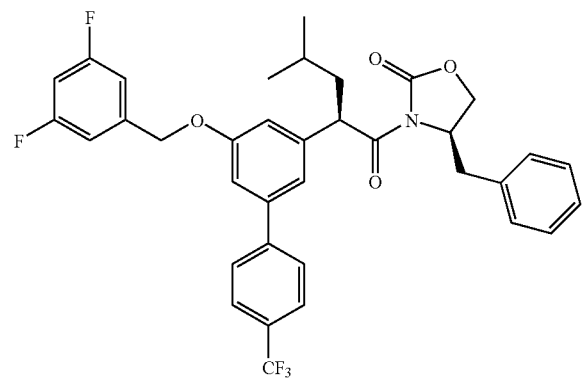

To a solution of 4-benzyl-3-[2-(5-hydroxy-4'-trifluoromethyl-biphenyl-3-yl)-4-methyl-pentanoyl]-oxazolidin-2-one (18.77 g, 36.73 mmol) in acetonitrile (184 mL) at 0° C. was added 1-bromomethyl-3,5-difluoro-benzene (7.13 mL, 55.10 mmol) and Cs$_2$CO$_3$ (23.94 g, 73.46 mmol) in portions over 5 minutes. The resulting white suspension was stirred at room temperature for 2 h. The white solid was filtered off and the solvent was removed in vacuo to obtain relatively pure 4-benzyl-3-{2-[5-(3,5-difluoro-benzyloxy)-4'-trifluoromethyl-biphenyl-3-yl]-4-methyl-pentanoyl}-oxazolidin-2-one.

m) 2-[5-(3,5-Difluoro-benzyloxy)-4'-trifluoromethyl-biphenyl-3-yl]-4-methyl-pentanoic acid

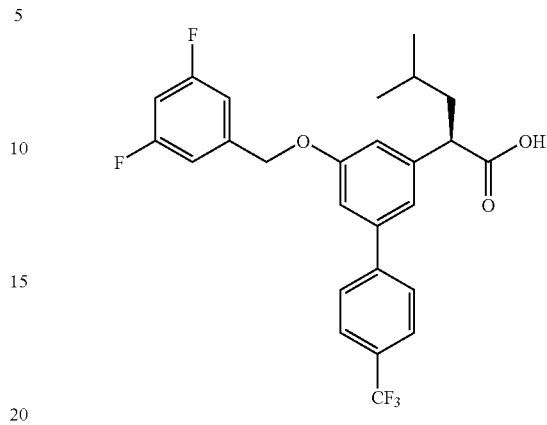

To a solution of 4-benzyl-3-{2-[5-(3,5-difluoro-benzyloxy)-4'-trifluoromethyl-biphenyl-3-yl]-4-methyl-pentanoyl}-oxazolidin-2-one (23.40 g, 36.73 mmol) in THF (180 mL) was added water (60 mL). The system was cooled to 0° C. To this cold solution was added LiOH.H$_2$O (1.54 g, 36.73 mmol) and 30% H$_2$O$_2$ (16.65 mL, 146.92 mmol), drop-wise, maintaining the internal temperature below 5° C. The resulting cloudy solution was stirred at 0° C. for 20 min. The excess H$_2$O$_2$ was quenched by adding 1.5 M aqueous Na$_2$SO$_3$ solution (97.9 mL, 146.92 mmol) and stirred at room temperature for 15 min. The organic solvent was removed in vacuo. The resulting liquid was acidified to pH 2 by adding 1 N aqueous HCl solution. The aqueous layer was extracted with EtOAc (3×200 mL), dried over MgSO$_4$, and concentrated in vacuo resulting in a crude mixture which was purified by ISCO silica gel column chromatography to yield (R)-2-[5-(3,5-difluoro-benzyloxy)-4'-trifluoromethyl-biphenyl-3-yl]-4-methyl-pentanoic acid (12.25 g, 70%).

$^1$H-NMR (CDCl$_3$): δ 0.93 (d, 6H), 1.51 (m, 1H), 1.72 (m, 1H), 1.98 (m, 1H), 3.72 (t, 1H), 5.09 (s, 2H), 6.76 (m, 1H), 6.98 (m, 3H), 7.07 (t, 1H), 7.17 (s, 1H), 7.66 (m, 4H); Calcd for C26H23F5O3 (M+H) 479.45, Found 479.2.

Example 2

(S)-2-[5-(3,5-Difluoro-benzyloxy)-4'-trifluoromethyl-biphenyl-3-yl]-4-methyl-pentanoic acid

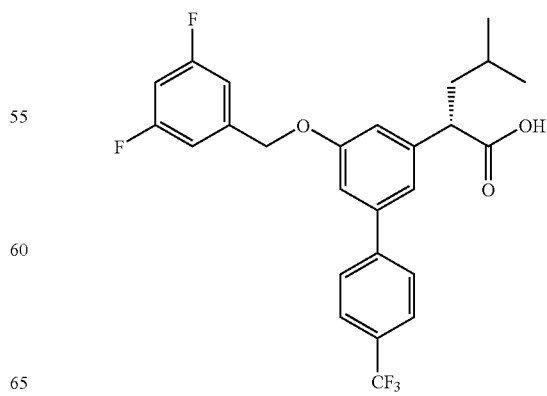

a) 4-Benzyl-3-[2-(5-hydroxy-4'-trifluoromethyl-biphenyl-3-yl)-4-methyl-pentanoyl]-oxazolidin-2-one

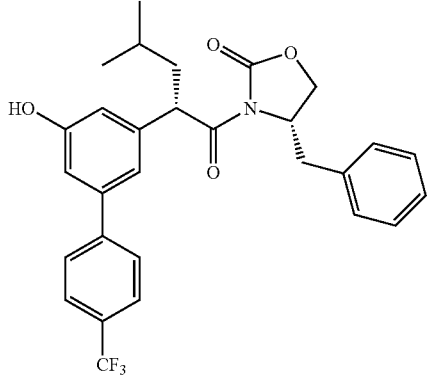

The title compound was prepared from 4-benzyl-3-[2-(5-benzyloxy-4'-trifluoromethyl-biphenyl-3-yl)-4-methyl-pent-4-enoyl]-oxazolidin-2-one following the same procedure as for the synthesis of Example 1, part (k).

$^1$H-NMR (CDCl$_3$): δ 0.94 (d, 3H), 0.98 (d, 3H), 1.54 (m, 1H), 1.74 (m, 1H), 2.12 (m, 1H), 2.79 (dd, 1H), 3.36 (dd, 1H), 4.11 (m, 2H), 4.62 (m, 1H), 5.25 (t, 1H), 6.97 (m, 2H), 7.21-7.37 (m, 6H), 7.67 (s, 4H); Calcd for C29H28F3NO4 (M+H) 512.20, Found 512.3.

b) 4-Benzyl-3-{2-[5-(3,5-difluoro-benzyloxy)-4'-trifluoromethyl-biphenyl-3-yl]-4-methyl-pentanoyl}-oxazolidin-2-one

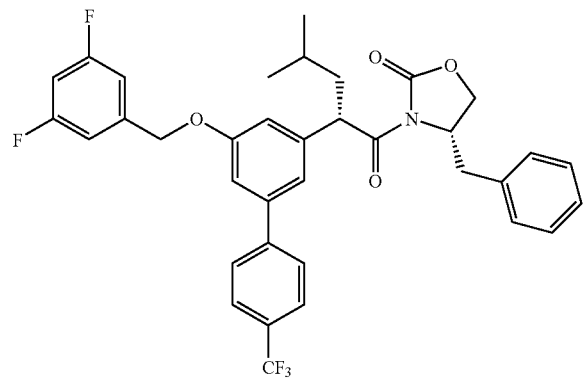

To a solution of 4-benzyl-3-[2-(5-hydroxy-4'-trifluoromethyl-biphenyl-3-yl)-4-methyl-pentanoyl]-oxazolidin-2-one (0.400 g, 0.78 mmol) in acetonitrile (3 mL) at room temperature was added 1-bromomethyl-3,5-difluoro-benzene (0.243 g, 1.17 mmol) and Cs$_2$CO$_3$ (0.508 g, 1.56 mmol). The resulting white suspension was stirred for 1 h. The white solid was filtered off and the solvent was removed in vacuo to obtain relatively pure 4-benzyl-3-{2-[5-(3,5-difluoro-benzyloxy)-4'-trifluoromethyl-biphenyl-3-yl]-4-methyl-pentanoyl}-oxazolidin-2-one.

c) 2-[5-(3,5-Difluoro-benzyloxy)-4'-trifluoromethyl-biphenyl-3-yl]-4-methyl-pentanoic acid

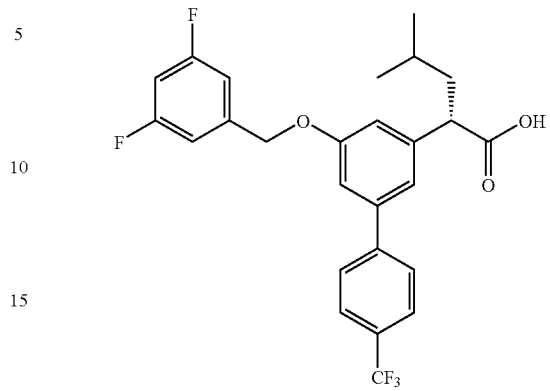

To a solution of 4-benzyl-3-{2-[5-(3,5-difluoro-benzyloxy)-4'-trifluoromethyl-biphenyl-3-yl]-4-methyl-pentanoyl}-oxazolidin-2-one (0.425 g, 0.67 mmol) in THF (10 mL) was added water (3.5 mL). The system was cooled to 0° C. To this cold solution was added LiOH.H$_2$O (0.028 g, 0.67 mmol) and 30% H$_2$O$_2$ (304 mL, 2.68 mmol), drop-wise, maintaining the internal temperature below 5° C. The resulting cloudy solution was stirred at 0° C. for 20 min. The excess H$_2$O$_2$ was quenched by adding 1.5 M aqueous Na$_2$SO$_3$ solution (1.79 mL, 2.68 mmol) and stirred at room temperature for 5 min. The organic solvent was removed in vacuo. The resulting liquid was acidified to pH 2 by adding 1 N aqueous HCl solution. The aqueous layer was extracted with EtOAc (3×25 mL) and dried (MgSO$_4$). The mixture was concentrated in vacuo to receive a crude mixture which was purified by ISCO silica gel column chromatography to yield (S)-2-[5-(3,5-difluoro-benzyloxy)-4'-trifluoromethyl-biphenyl-3-yl]-4-methyl-pentanoic acid (0.295 g, 92%).

$^1$H-NMR (CDCl$_3$): δ 0.93 (d, 6H), 1.51 (m, 1H), 1.72 (m, 1H), 1.98 (m, 1H), 3.72 (t, 1H), 5.09 (s, 2H), 6.76 (m, 1H), 6.98 (m, 3H), 7.07 (t, 1H), 7.17 (s, 1H), 7.66 (m, 4H); Calcd for C26H23F5O3 (M+H) 479.45, Found 479.2.

Example 3

(R)-2-[5-(4-fluoro-2-trifluoromethyl-benzyloxy)-4'-trifluoromethyl-biphenyl-3-yl]-4-methyl-pentanoic acid

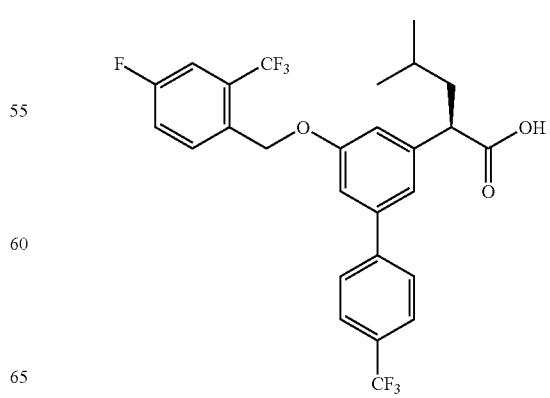

a) 4-Benzyl-3-{2-[5-(4-fluoro-2-trifluoromethyl-benzyloxy)-4'-trifluoromethyl-biphenyl-3-yl]-4-methyl-pentanoyl}-oxazolidin-2-one

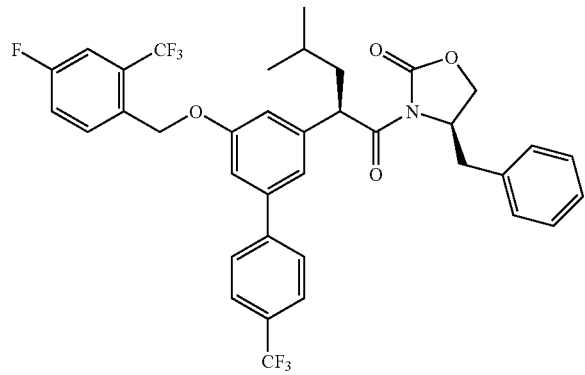

To a solution of 4-benzyl-3-[2-(5-hydroxy-4'-trifluoromethyl-biphenyl-3-yl)-4-methyl-pentanoyl]-oxazolidin-2-one (as prepared in Example 1, step (k))(0.400 g, 0.78 mmol) in acetonitrile (3.9 mL) was added 1-bromomethyl-4-fluoro-2-trifluoromethyl-benzene (0.181 mL, 1.17 mmol) and $Cs_2CO_3$ (0.508 g, 1.56 mmol). The resulting white suspension was stirred at room temperature for 1 h. The white solid was filtered off and the solvent was removed in vacuo to obtain relatively pure 4-benzyl-3-{2-[5-(4-fluoro-2-trifluoromethyl-benzyloxy)-4'-trifluoromethyl-biphenyl-3-yl]-4-methyl-pentanoyl}-oxazolidin-2-one.

b) 2-[5-(4-Fluoro-2-trifluoromethyl-benzyloxy)-4'-trifluoromethyl-biphenyl-3-yl]-4-methyl-pentanoic acid

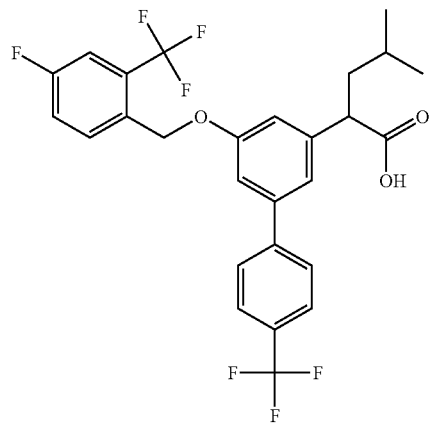

To a solution of 4-benzyl-3-{2-[5-(4-fluoro-2-trifluoromethyl-benzyloxy)-4'-trifluoromethyl-biphenyl-3-yl]-4-methyl-pentanoyl}-oxazolidin-2-one (0.535 g, 0.78 mmol) in THF (9 mL) was added water (3 mL). The system was cooled to 0° C. To this cold solution was added $LiOH.H_2O$ (33 mg, 0.78 mmol) and 30% $H_2O_2$ (0.354 mL, 3.12 mmol,) and stirred at 0° C. for 20 min. The excess $H_2O_2$ was quenched by adding 1.5 M aqueous $Na_2SO_3$ solution (2.08 mL, 3.12 mmol) and stirred at room temperature for 5 min. The organic solvent was removed in vacuo. The resulting liquid was acidified to pH 2 by adding 1 N aqueous HCl solution. The aqueous layer was extracted with EtOAc (3×50 mL) and dried ($MgSO_4$). The mixture was concentrated in vacuo to receive a crude mixture which was purified by ISCO silica gel column chromatography to yield (R)-2-[5-(4-Fluoro-2-trifluoromethyl-benzyloxy)-4'-trifluoromethyl-biphenyl-3-yl]-4-methyl-pentanoic acid (310 mg).

$^1$H-NMR (CDCl$_3$): δ 0.92 (d, 6H), 1.52 (m, 1H), 1.71 (m, 1H), 1.99 (m, 1H), 3.73 (t, 1H), 5.27 (s, 2H), 6.98 (bs, 1H), 7.06 (bs, 1H), 7.17 (bs, 1H), 7.29 (m, 1H), 7.42 (m, 1H), 7.68 (m, 5H); Calcd for C27H23F7O3 (M+H) 529.46, Found 529.2.

Example 4

2-[4'-Chloro-5-(3,5-difluoro-2-benzyloxy)-3'-trifluoromethyl-biphenyl-3-yl]-4-methyl-pentanoic acid

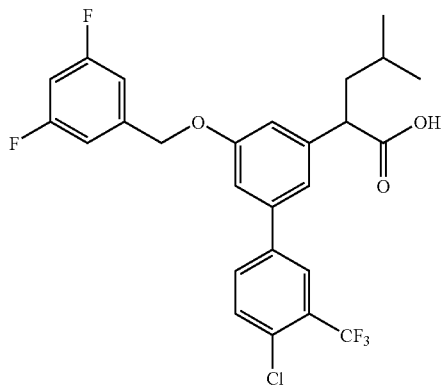

a) 2-(3,5-Bis-benzyloxy-phenyl)-4-methyl-pent-4-enoic acid methyl ester

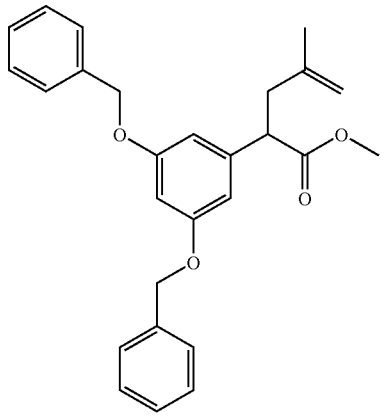

A 2M solution of LDA in THF-heptane-ethylbenzene (21.5 mL, 43.0 mmol) was added dropwise over 12 min to a stirred solution of (3,5-bis-benzyloxyphenyl)acetic acid methyl ester (prepared in Example 1, step (a)) (13.0 g, 35.9 mmol) in THF (80 mL) at −78° C. under a nitrogen atmosphere. The temperature was maintained below −70° C. for an additional 50 min, then 3-bromo-2-methylpropene (4.0 mL, 39.7 mmol) was added in one portion and the reaction mixture was warmed to 0° C. After 2 h the mixture was concentrated in vacuo, diluted with sat. aq. NH$_4$Cl (100 mL) and extracted with EtOAc (100 mL). The organic layer was washed with brine (100 mL), dried (MgSO$_4$), concentrated in vacuo and purified by flash chromatography (silica, 0-10% EtOAc in petroleum ether) to afford the title product as a yellow oil (14.1 g, 94%). $^1$H-NMR (400 MHz, CDCl$_3$): δ7.42-7.25 (m, 10H), 6.58 (s, 2H), 6.52 (s, 1H), 5.02 (s, 4H), 4.74 (s, 1H), 4.66 (s, 1H), 3.74 (t, 1H), 3.64 (s, 3H), 2.79 (dd, 1H), 2.38 (dd, 1H), 1.70 (s, 3H).

b) 2-(3-Benzyloxy-5-hydroxy-phenyl)-4-methyl-pentanoic acid ethyl ester

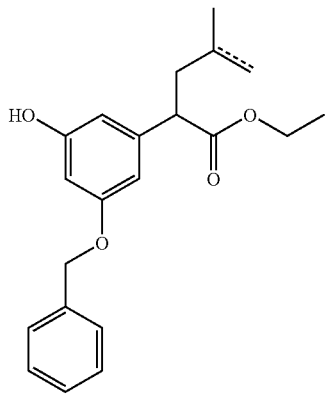

A mixture of intermediate 4a (20 g, 48 mmol), NaOH (2.3 g, 57 mmol) in EtOH (500 mL) was added 0.5 g Pd—C 10% on activated carbon under $N_2$, the mixture was subjected to hydrogenation under 40 psi for 30 min, at which point LC/MS indicated that the starting material was consumed. The catalyst was filtered out and EtOH was evaporated. Column chromatography (0-40% EtOAc/Heptane) gave 11.8 g (75% yield) colorless oil, as a mixture of methyl and ethyl esters and the unreduced double bond ester. $MH^+$ 341 (Ethyl ester with unreduced double bond); 343 (ethyl ester with reduced isopropyl branch); 327 (methyl ester with unreduced double bond).

c) 2-[3-Benzyloxy-5-(3,5-difluoro-benzyloxy)-phenyl]-4-methyl-pentanoic acid ethyl ester

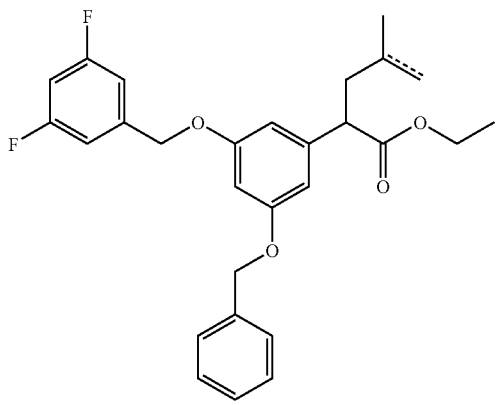

A solution of ethyl ester (mixed with methyl ester) 4b (5 g, 15 mmol), $K_2CO_3$ (4.1 g, 30 mmol), and 3,5 di-fluoro benzyl bromide (2.9 mL, 22 mmol) in DMF (70 mL) was heated to 80° C. for one hour. DMF was removed by vacuum and the crude product was purified by column chromatography (0-30% EtOAc/heptane) to give 4.5 g product (66% yield). $MH^+$ 453.1 and other molecular ions (methyl ester and the corresponding olefins).

d) 2-[3-(3,5-Difluoro-benzyloxy)-5-trifluoromethanesulfonyloxy-phenyl]-4-methyl-pentanoic acid ethyl ester

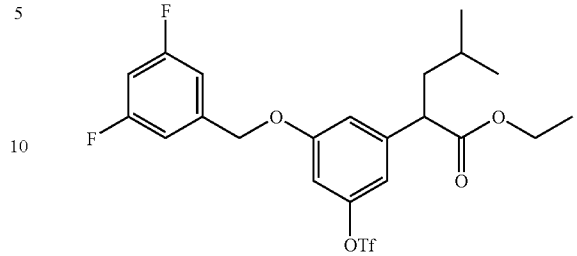

To a solution of intermediate 4c (4.5 g, 10 mmol) in MeOH (100 mL) was added 0.45 g Pd—C 10% on activated carbon under $N_2$; the mixture was subjected to hydrogenation under 20 psi for two hours. The catalyst was filtered out and MeOH was evaporated. Column chromatography (0-50% EtOAc/Heptane) gave 3.0 g phenol as colorless oil, which was dissolved in 50 mL of DCM and cooled to 0° C. Pyridine (2 mL, 40 mmol) and trifluoromethanesulfonic acid anhydride (2 mL, 12 mmol) was added. The solution was stirred at 0° C. for one hour before being poured it into 1N HCl solution (20 mL), extracted with DCM (200 mL), and washed by $NaHCO_3$/NaCl aq. The DCM layer was dried over $Mg_2SO_4$ and evaporated to give 4.0 g yellow oil. (78% two steps). $MH^+$ 511.2 e) 2-[4'-Chloro-5-(3,5-difluoro-benzyloxy)-3'-trifluoromethyl-biphenyl-3-yl]-4-methyl-pentanoic acid ethyl ester

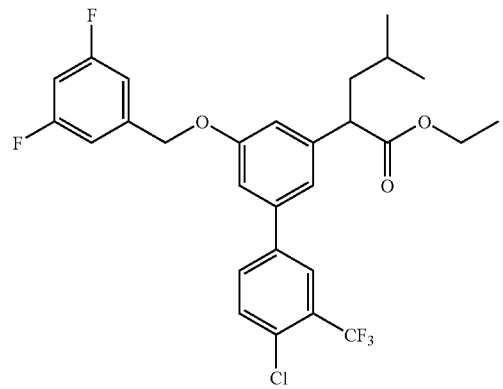

A solution of 3-$CF_3$-4-Cl-benzenboronic acid (3.6 g, 16 mmol), triflate 4d (4 g, 7.8 mmol), $(PPh_3)_4Pd$ (0.5 g, 0.4 mmol), $K_2CO_3$ (2.2 g, 16 mmol), in toluene/EtOH/$H_2O$ (20/10/5 mL) was placed in a sealed reaction tube and heated to 80° C. for one hour. EtOAc (200 mL) added and washed with brine. The EtOAc layer was dried over $Mg_2SO_4$ and evaporated. Column chromatography (0-20%/EtOAc/Hexane) yielded 3.05 g colorless oil (74%). $MH^+$ 541.3 f) 2-[4'-Chloro-5-(3,5-difluoro-2-benzyloxy)-3'-trifluoromethyl-biphenyl-3-yl]-4-methyl-pentanoic acid A solution of intermediate 4e (3 g, 5.5 mmol), 1N NaOH (16 mL) in THF/MeOH (50/50 mL) was stirred at room temperature for one day. The solution was concentrated and EtOAc (500 mL) was added. After washing with 1N HCl and brine., the EtOAc layer was dried over $Mg_2SO_4$ and evaporated. Column chromatography (0-30%/EtOAc/Hexane) yielded 2.7 g white solid (71%). The solid was then dissolved in EtOAc (100 mL) and added to 1N NaOH (5.26 mL, 5mmol) and stirred at room temperature for 10 min. The solvent was then removed by vacuum and compound was obtained as its sodium salt. MH 513.2 (weak peak). $^1$H NMR (300 MHz, CD$_3$OD): δ0.94 (d, 6H, J=6.51 Hz), δ1.5-1.67 (m, 2H), δ1.9-2.0 (m, 1H), δ3.67 (t, 1H, J=7.85 Hz), δ5.2 (s, 2H), δ6.89 (m, 1H), δ7.1 (m, 4H), δ7.27 (s, 1H), δ7.68 (d, 1H, J=8.42 Hz), δ7.85 (m, 1H), δ7.97 (d, 1H, J=2.0 Hz).

Determination of the Effect of the Compounds According to the Invention on Cyclooxygenase-1 and Cyclooxygenase-2 (Cox-1, Cox-2)

Inhibition of Cox-1 and Cox-2 was determined using the Colorimetric Cox inhibitor screening assay provided by Cayman Chemical Company, Ann Arbor, Mich., USA. (Cat. No. 760111) according to manufacturer's instructions.

Example 1 of the invention shows <50% inhibition at 100 μM.

Screening of the Compounds of the Invention for γ-Secretase-Modulating Activity

Screening was carried out using SKNBE2 cells carrying the APP 695-wild type, grown in DMEM/NUT-mix F12 (HAM) provided by Gibco (cat no. 31330-38) containing 5% Serum/Fe supplemented with 1% non-essential amino acids.

Cells were grown to near confluency.

The screening was performed using the assay as described in Citron et al (1997) Nature Medicine 3: 67.

| Structure | | EC50 in WTAPP cell assay Aβ42 (uM) |
|---|---|---|
| 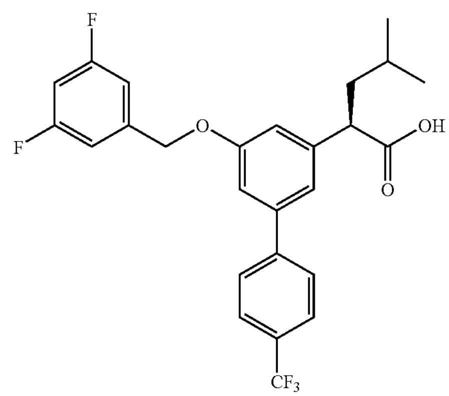 | Compound 1 | 0.525 |
| 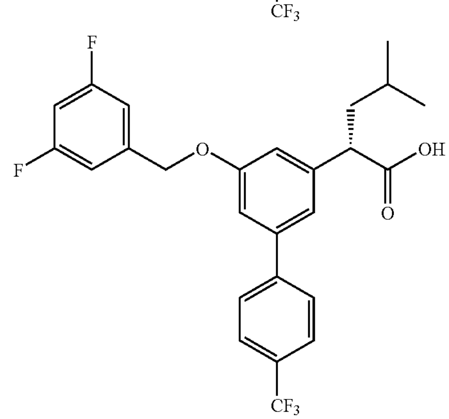 | Compound 2 | 1.123 |
| 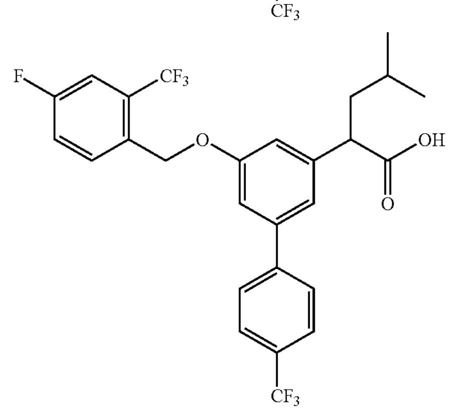 | Compound 3 | 0.316 |

-continued

| Structure | | EC50 in WTAPP cell assay Aβ42 (uM) |
|---|---|---|
| 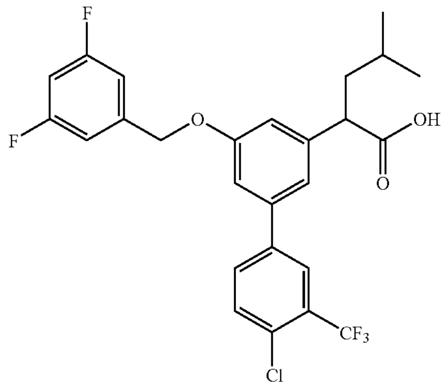 | Compound 4 | 0.19 |

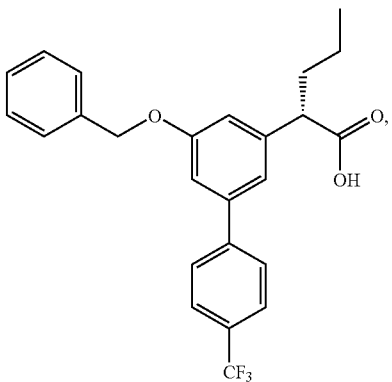

which features neither the selected R¹ and R² values, nor the sec-butyl group, displayed an $IC_{50}$ of 2.5 µM in the above WTAPP cell assay.

Demonstration of in vivo Efficacy

Aβ42 lowering agents of the invention can be used to treat AD in mammals such as humans or alternatively demonstrating efficacy in animal models such as, but not limited to, the mouse, rat, or guinea pig. The mammal may not be diagnosed with AD, or may not have a genetic predisposition for AD, but may be transgenic such that it overproduces and eventually deposits Aβ in a manner similar to that seen in humans afflicted with AD.

Aβ42 lowering agents can be administered in any standard form using any standard method. For example, but not limited to, Aβ42 lowering agents can be in the form of liquid, tablets or capsules that are taken orally or by injection. Aβ42 lowering agents can be administered at any dose that is sufficient to significantly reduce levels of Aβ42 in the blood, blood plasma, serum, cerebrospinal fluid (CSF), or brain.

To determine whether acute administration of an Aβ42 lowering agent would reduce Aβ42 levels in vivo, non-transgenic rodents, e.g. mice or rats were used. Alternatively, two to three month old Tg2576 mice expressing APP695 containing the "Swedish" variant can be used or a transgenic mouse model developed by Dr. Fred Van Leuven (K. U. Leuven, Belgium) and co-workers, with neuron-specific expression of a clinical mutant of the human amyloid precursor protein [V717I] (Moechars et al., 1999 J. Biol. Chem. 274, 6483). Young transgenic mice have high levels of Aβ in the brain but no detectable Aβ deposition. At approximately 6-8 months of age, the transgenic mice start to display spontaneous, progressive accumulation of β-amyloid (Aβ) in the brain, eventually resulting in amyloid plaques within the subiculum, hippocampus and cortex. Animals treated with the Aβ42 lowering agent will be examined and compared to those untreated or treated with vehicle and brain levels of soluble Aβ42 and total Aβ would be quantitated by standard techniques, for example, using ELISA. Treatment periods may vary from hours to days and will be adjusted based on the results of the Aβ42 lowering once a time course of onset of effect can be established.

A typical protocol for measuring Aβ42 lowering in vivo is shown but it is only one of many variations that could be used to optimize the levels of detectable Aβ. For example, Aβ42 lowering compounds as free acids or sodium salts were formulated in 5% of solutol in water or 20% hydroxypropyl β cyclodextrin. The Aβ42 lowering agents are administered as a single oral dose or by any acceptable route of administration e.g., three to four hours before sacrifice, determined empirically, and analysis or alternatively could be given over a course of days and the animals sacrificed three to four hours after the final dose is given.

The mice are anaesthetized with a mixture of Ketalar (Ketamin), Rompun (Xylazin 2%) and Atropin (2:1:1) and flushed trans-cardially with physiological serum at 4° C. Blood is collected at sacrifice. The blood collection is performed via a heart puncture during anesthesia in EDTA treated collection tubes. Blood is centrifuged at 4000 g for 5 minutes at 4° C. and the plasma recovered and flash frozen for later analysis. The brain is removed from the cranium and hindbrain and forebrain are separated with a cut in the coronal/frontal plane.

The cerebellum is removed and retained for quantitative analysis of test compound levels. The forebrain is divided evenly into left and right hemisphere by using a midline sagital cut.

Both hemispheres are immediately immersed in liquid nitrogen and stored at −70° C. until homogenization for biochemical assays.

Mouse brains are resuspended in 10 volumes of 0.4% DEA (diethlyamine)/50 mM NaCl pH 10 (for non-transgenic animals) or 0.1% CHAPS in TBS (for transgenic animals) containing protease inhibitors (Roche-11948699) per gram of tissue, e.g. for 0.158 g brain, add 1.58 ml of 0.4% DEA. All samples are sonicated for 30 seconds on ice at 30% power output. Homogenates are centrifuged at 355,000×g for 30 min. The resulting high speed supernatants are then transferred to fresh tubes for subsequent purification or immediated assay.

The obtained supernatants are purified with Water Oasis HLB reverse phase columns (Waters Corp., Milford, Mass.) to remove non-specific immunoreactive material from the brain lysates prior subsequent Aβ detection. Using a vacuum manifold, all solutions were passed through the columns at a rate of approximately 1 mL per minute, so the vacuum pressure was adjusted accordingly throughout the procedure. Columns were preconditioned with 1 mL of 100% MeOH, before equilibration with 1 mL of $H_2O$. Non-neutralized brain lysates were loaded on to the columns. The loaded samples were then washed twice with the first wash performed with 1 mL of 5% MeOH, and the second wash with 1 mL of 30% MeOH. Finally, the Aβ was eluted from the columns and into 100×30 mm glass tubes, with a solution of 90% MeOH with 2% $NH_4OH$. The eluate was then transferred into 1.5 mL tubes and concentrated in a speed-vac concentrator on high heat for about 2 hours. The concentrated Aβ was then resuspended in UltraCULTURE General Purpose Serum-Free Medium (Cambrex Corp., Walkersville, Md.) plus Protease Inhibitors added according to the manufacturers recommendation.

To quantify the amount of Aβ42 in the soluble fraction of the brain homogenates, commercially available Enzyme-Linked-Immunosorbent-Assay (ELISA) kits are used (Innotest® β-Amyloid$_{(1-42)}$, Innogenetics N.V., Ghent, Belgium). The Aβ42 ELISA is performed essentially according to the manufacturer's protocol. Briefly, the standard (a dilution of synthetic Aβ1-42) and samples are prepared on a 96-well polypropylene pre-coated plate supplied with the kit(Nunc-Immuno MaxiSorp, A/S Nunc, Denmark). The standard dilutions with final concentrations of 1000, 500, 250, 125, 62.5, 31.3 and 15.6 pg/ml and the samples are prepared in the sample diluent, furnished with the ELISA kit, to a final volume of 60 μl. Samples, standards and blanks (50 μl) are added to the anti-Aβ42-coated plate (the capture antibody selectively recognizes the C-terminal end of the antigen). The plate is allowed to incubate overnight at 4° C. in order to allow formation of the antibody-amyloid complex. Following this incubation and subsequent wash steps a selective anti-Aβ-antibody conjugate (biotinylated detection antibody, e.g., biotinylated 4G8 (Covance Research Products, Dedham, Mass.) is added and incubated for a minimum of 1 hour in order to allow formation of the antibody-Amyloid-antibody-complex. After incubation and appropriate wash steps, a Streptavidine-Peroxidase-Conjugate is added, followed 30 minutes later by an addition of TMB/peroxide mixture, resulting in the conversion of the substrate into a colored product. This reaction is stopped by the addition of sulfuric acid (1M) and the color intensity is measured by means of photometry with an ELISA-reader with a 450 nm filter. Quantification of the Aβ content of the samples is obtained by comparing absorbance to a standard curve made with synthetic Aβ1-42. Alternatively, detection can be achieved using the Pierce QuantBlu Fluorogenic Peroxidase Substrate and Detection reagents according to the manufacturers instructions (Pierce Corp., Rockford, Ill.).

In such a model at least 20% Aβ42 lowering compared to untreated animals would be advantageous.

In Vivo Data

Oral dose 30 mg/kg at 4 hr Time Point

| Structure | | In vivo mouse Aβ42 efficacy @ 30 mpk (4 hr) inhibition | Brain/plasma concentration @ 30 mpk po (4 hr) |
|---|---|---|---|
| 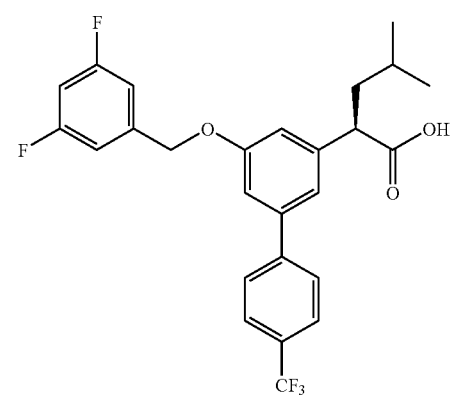 | Compound 1 | 50% | 6.9 ± 2.3 uM/ 45 ± 12.2 uM |

| Structure | | In vivo mouse Aβ42 efficacy @ 30 mpk (4 hr) inhibition | Brain/plasma concentration @ 30 mpk po (4 hr) |
|---|---|---|---|
| (structure of Compound 2: 3,5-difluorobenzyloxy-substituted biphenyl with 4-CF3, isobutyl carboxylic acid) | Compound 2 | 45% | 11.1 ± 2.8 uM/ 43.3 ± 8.9 uM |
| (structure of Compound 3: 4-fluoro-2-trifluoromethylbenzyloxy-substituted biphenyl with 4-CF3, isobutyl carboxylic acid) | Compound 3 | 25% | 5.1 ± 1.1 uM/ 18.4 ± 2.8 uM |
| (structure of Compound 4: 3,5-difluorobenzyloxy-substituted biphenyl with 3-CF3, 4-Cl, isobutyl carboxylic acid) | Compound 4 | 42% | 6.5 ± 1.5 uM/ 24.5 ± 6.3 uM |

By comparison,

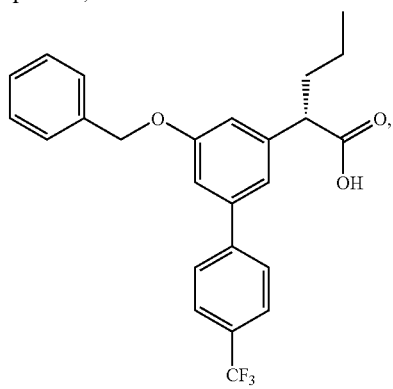

required dosing of 100 mpk BID in order to lower Aβ42 plasma levels in mouse by 40%.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All publications disclosed in the above specification are hereby incorporated by reference in full.

I claim:

1. A compound of Formula I:

(Formula I)

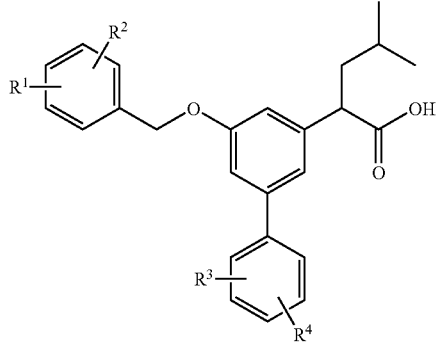

wherein:
$R^1$ is F, Cl, or $CF_3$;
$R^2$ is F, Cl, or $CF_3$;
$R^3$ is F, Cl, or $CF_3$
$R^4$ is H, F, Cl, or $CF_3$;
and pharmaceutically acceptable salts thereof.

2. A compound of claim 1 wherein:
$R^1$ is F;
$R^3$ is $CF_3$;
and pharmaceutically acceptable salts thereof.

3. A compound of claim 2 selected from the group consisting of:
(R)-2-[5-(3,5-Difluoro-benzyloxy)-4'-trifluoromethyl-biphenyl-3-yl]-4-methyl-pentanoic acid, (S)-2-[5-(3,5-Difluoro-benzyloxy)-4'-trifluoromethyl-biphenyl-3-yl]-4-methyl-pentanoic acid, 2-[5-(4-Fluoro-2-trifluoromethyl-benzyloxy)-4'-trifluoromethyl-biphenyl-3-yl]-4-methyl-pentanoic acid, 2-[4'-Chloro-5-(3,5-difluoro-benzyloxy)-3'-trifluoromethyl-biphenyl-3-yl]-4-methyl-pentanoic acid, and pharmaceutically acceptable salts thereof.

4. A compound according to any of claims 1 to 3 for use as a medicament.

5. A pharmaceutical composition comprising a compound according to any of claims 1 to 3 in admixture with an inert carrier.

6. A method of treating Alzheimer's disease in a mammal, which method comprises administering to said mammal a therapeutically effective amount of a compound according to any of claims 1 to 3.

* * * * *

UNITED STATES PATENT AND TRADEMARK OFFICE
Certificate

Patent No. 7,897,643 B2                                          Patented: March 1, 2011

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Chih Yung Ho, Lansdale, PA (US); Umar S. M. Maharoof, North Wales, PA (US); Jeremy Major, Fulbourn (UK); and John Harrison, Cambridge (UK).

Signed and Sealed this Nineteenth Day of February 2013.

WU-CHENG WINSTON SHEN
*Supervisory Patent Examiner*
Art Unit 1621
Technology Center 1600